United States Patent
Nandedkar et al.

(10) Patent No.: US 10,994,313 B2
(45) Date of Patent: May 4, 2021

(54) SANITARY STORAGE OF THERMAL THERAPEUTIC WRAPS

(71) Applicant: Solid State Cooling Systems, Inc., Wappingers Falls, NY (US)

(72) Inventors: Vishesh Nandedkar, Poughkeepsie, NY (US); Lloyd Wright, Hopewell Junction, NY (US)

(73) Assignee: Solid State Cooling Systems, Inc., Wappingers Falls, NY (US)

( * ) Notice: Subject to any disclaimer, the term of this patent is extended or adjusted under 35 U.S.C. 154(b) by 61 days.

(21) Appl. No.: 16/356,865

(22) Filed: Mar. 18, 2019

(65) Prior Publication Data

US 2019/0217347 A1    Jul. 18, 2019

Related U.S. Application Data

(63) Continuation-in-part of application No. 15/867,238, filed on Jan. 10, 2018.

(Continued)

(51) Int. Cl.
    *B08B 7/00*    (2006.01)
    *A61F 7/02*    (2006.01)
(Continued)

(52) U.S. Cl.
CPC ............ *B08B 7/0057* (2013.01); *A61B 90/70* (2016.02); *A61F 7/0085* (2013.01); *A61F 7/02* (2013.01);
(Continued)

(58) Field of Classification Search
CPC ..... B08B 7/0057; B08B 7/0071; A61B 90/70; A61B 2090/064; A61B 2090/065; A61B 90/98; A61F 7/0085; A61F 7/02; A61F 2007/0002; A61F 2007/0032; A61F 2007/0034; A61F 2007/0042; A61F 2007/0054; A61F 2007/0056; A61F 2007/0076; A61F 2007/0092; A61F 2007/0093; A61F 2007/0096; A61F 2007/0295; A61F 2007/0296; A61F 7/007; A61F 7/00; A61F 2007/0094; A61F 2007/0027; A61F 2007/0225; A61F 2007/0282; A61F 2007/0086; A61L 2/10; A61L 2/26; A61L 2202/11;

(Continued)

(56) References Cited

U.S. PATENT DOCUMENTS 5,072,875 A * 12/1991 Zacoi ..................... A61F 7/02
                                             607/104
2008/0071330 A1   3/2008 Quisenberry et al.
(Continued)

Primary Examiner — Xiuyu Tai
(74) Attorney, Agent, or Firm — Rogers Towers, P.A.; Joseph P. Kincart

(57) ABSTRACT

A system including apparatus and methods for sanitizing or otherwise reducing biologics present on thermal therapeutic treatment wraps used for treating athletes after workouts or games, physical therapy patients after injury, and hospital patients after surgery is disclosed. The system includes a storage cabinet with an internal conveyor system that exposes each wrap to periodic sanitization or other biologic reduction means, such as ultraviolet light. This prevents growth of bacteria and mold. In some embodiments, warm air is blown into the storage cabinet to assist with drying the wraps.

10 Claims, 16 Drawing Sheets

Related U.S. Application Data

(60) Provisional application No. 62/444,416, filed on Jan. 10, 2017.

(51) Int. Cl.

| | | |
|---|---|---|
| *A61L 2/10* | (2006.01) | |
| *A61L 2/26* | (2006.01) | |
| *A61F 7/00* | (2006.01) | |
| *A61N 5/06* | (2006.01) | |
| *A61B 90/70* | (2016.01) | |
| *A61N 2/00* | (2006.01) | |
| *A61B 90/00* | (2016.01) | |
| *A61B 90/98* | (2016.01) | |

(52) U.S. Cl.
CPC .................. *A61L 2/10* (2013.01); *A61L 2/26* (2013.01); *A61N 2/002* (2013.01); *A61N 5/0619* (2013.01); *A61N 5/0624* (2013.01); *A61N 5/0625* (2013.01); *A61B 90/98* (2016.02); *A61B 2090/064* (2016.02); *A61B 2090/065* (2016.02); *A61F 2007/0002* (2013.01); *A61F 2007/0032* (2013.01); *A61F 2007/0034* (2013.01); *A61F 2007/0042* (2013.01); *A61F 2007/0054* (2013.01); *A61F 2007/0056* (2013.01); *A61F 2007/0076* (2013.01); *A61F 2007/0092* (2013.01); *A61F 2007/0093* (2013.01); *A61F 2007/0096* (2013.01); *A61F 2007/0295* (2013.01); *A61F 2007/0296* (2013.01); *A61L 2202/11* (2013.01); *A61L 2202/14* (2013.01); *A61L 2202/24* (2013.01); *A61N 2/008* (2013.01); *A61N 5/062* (2013.01); *A61N 5/0622* (2013.01); *A61N 2005/0626* (2013.01); *A61N 2005/0645* (2013.01); *A61N 2005/0659* (2013.01); *A61N 2005/0661* (2013.01); *B08B 7/0071* (2013.01)

(58) Field of Classification Search
CPC . A61L 2202/14; A61L 2202/24; A61N 2/002; A61N 5/0619; A61N 5/0624; A61N 5/0625; A61N 2/008; A61N 5/062; A61N 5/0622; A61N 2005/0626; A61N 2005/0645; A61N 2005/0659; A61N 2005/0661; A61N 1/0484; A61N 1/36021; A61N 1/0492

See application file for complete search history.

(56) References Cited

U.S. PATENT DOCUMENTS

| | | |
|---|---|---|
| 2013/0238042 A1 | 9/2013 | Gildersleeve et al. |
| 2014/0222121 A1 | 8/2014 | Spence et al. |
| 2015/0118107 A1* | 4/2015 | Sunkara ................ A61B 90/98 422/24 |
| 2015/0335468 A1 | 11/2015 | Rose et al. |
| 2016/0242957 A1 | 8/2016 | Schaefer et al. |
| 2017/0348449 A1* | 12/2017 | Ward ....................... A61L 2/18 |

* cited by examiner

SANITARY STORAGE OF THERMAL THERAPEUTIC WRAPS

CROSS-REFERENCE TO RELATED APPLICATIONS

The present application claims priority to U.S. Non-provisional patent application Ser. No. 15/867,238, filed Jan. 10, 2018, and entitled "Accelerated Transition Thermal Contrast Therapy Device," as a Continuation-in-Part Application; which in turn claims priority to Provisional Patent Application Ser. No. 62/444,416, filed Jan. 1, 2017 entitled "Accelerated Transition Thermal Contrast Therapy Device". The contents of both of which are relied upon and hereby incorporated by reference.

FIELD OF THE INVENTION

The present invention relates to a system, methods, and apparatus for sanitary storage and treatment of thermal therapy treatment wraps to prevent mold and bacterial growth.

BACKGROUND OF THE INVENTION

Thermal contrast therapy has risen in popularity in recent years. Application of thermal contrast therapy typically involves application of cycles of heat and cooling combined with compression to a localized site on a patient. Of course the close contact and interaction with a human or other mammalian patient introduces bacteria onto a surface of a device used for application of the thermal contrast therapy. In addition, one popular application of thermal contrast therapy includes patients that are athletes. The athletes will often sweat and introduce moisture onto the thermal contrast therapy device. The moisture is conducive to growth of bacteria and mold on the thermal contrast device, on indeed any thermal therapeutic device.

In order to address the exposure of a patient to bacteria and mold or other biological contaminant, cleaning and/or sterilization of a device, such as a thermal contrast wrap, used to administer the thermal contrast therapy are needed.

Applicant has previously submitted U.S. patent application Ser. No. 15/867,238, entitled Accelerated Transition Thermal Contrast Therapy Device (the "'238 Application"), which is directed to thermal therapy treatment wraps that address these issues. The contents of the '238 Application are incorporated by reference and relied upon in the present disclosure.

The wraps disclosed in the '238 Application, along with many general thermal therapeutic medical wraps, may be exposed to mold and bacterial growth. Athletic trainers, physical therapists, and doctors commonly apply flexible, plastic, water-cooled, or heated wraps to areas of a patient's body to treat muscles, tendons, and ligaments after strenuous exercise, injury, or surgery. Often, these wraps are reused many times, even by multiple different patients. While the wraps are stored between uses, gray mold and bacteria may have an opportunity to grow and thrive on the wraps' fertile plastic surfaces, which is undesirable.

SUMMARY OF THE INVENTION

Accordingly, the present invention provides a solution for storing thermal therapy treatment wraps without allowing mold to grow. Moreover, the present invention provides methods and apparatus for treating a thermal therapy treatment wrap to sanitize or otherwise reduce biological life located on the wrap.

According to the present invention, a storage cabinet with an internal conveyor system exposes each wrap to periodic treatment, such as UV light and/or other wavelength of radiation, steam, chemical immersion or other treatment aimed at reducing the presence of such biological organisms on the wrap and preventing growth of bacteria and mold. In some embodiments the treatment is effective to disinfect and/or sterilize the thermal therapy treatment wraps.

In some embodiments, a portion of a thermal therapy treatment wraps is separated from the thermal therapy treatment wrap unit and processed via the methods and apparatus described herein to reduce biologic organism present on the portion of the wrap. For example, in some embodiments, a liner, sleeve or other intermediary layer may be separated and processed.

Various features and embodiments are further described in the following figures, drawings and claims.

BRIEF DESCRIPTION OF THE DRAWINGS

As presented herein, various embodiments of the present invention will be described, followed by some specific examples of various components that can be utilized to implement the embodiments. The following drawings facilitate the description of some embodiments of the present invention.

Figure 1:
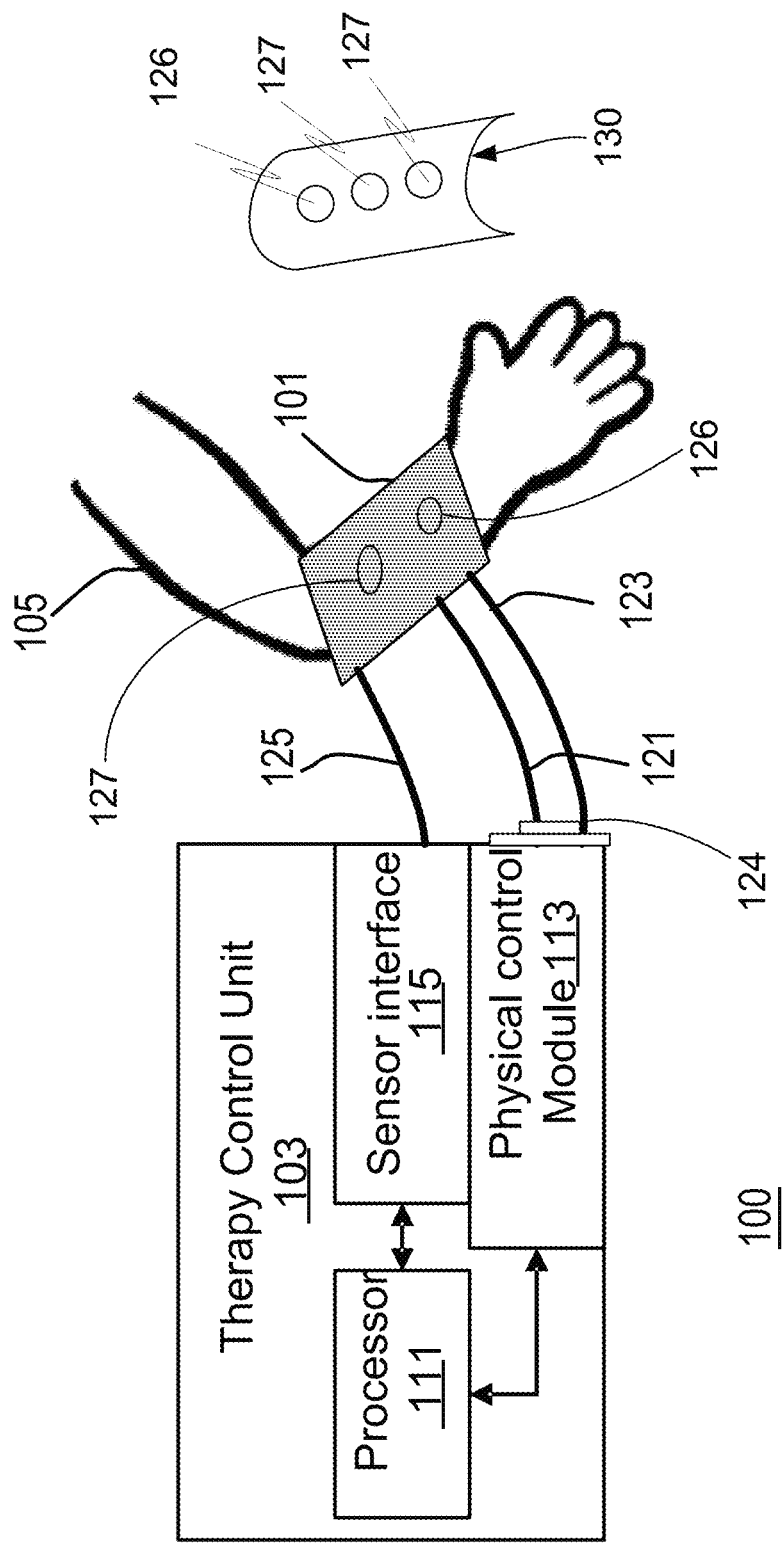
FIG. 1 illustrates at a relatively high level of abstraction a thermal contrast therapy system according to some exemplary embodiments of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The present invention provides apparatus and methods for sanitary storage and treatment of thermal therapeutic wraps. Throughout this disclosure, "thermal therapeutic wraps," "thermal therapy wraps," "thermal wraps," and "wraps" may be used interchangeably. The subject matter of the '238 Application, thermal contrast therapeutic wraps, represents a subset of thermal wraps. According to the present invention, thermal therapeutic wraps may be cyclically exposed to a sanitization source device.

As used herein, "sanitize" may mean generally to make clean or hygienic, disinfect, or otherwise remove biologics from a surface.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted that the examples presented herein should not be construed as limiting of the scope of embodiments of the present disclosure, as other equally effective examples are possible and likely.

As used herein, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing sets of computer code in a processor that performs the function; providing provisionable configuration parameters that control, limit, enable or disable capabilities of the module (e.g., setting a flag, setting permissions, setting threshold levels used at decision points, etc.); providing or removing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; setting a value of an adjustable component (e.g., a tunable resistance or capacitance, etc.), energizing a circuit that performs the function (e.g., providing power to a transceiver circuit in order to receive data); providing the module in a physical size that inherently performs the function (e.g., an RF antenna whose gain and operating frequency range is determined or constrained by the physical size of the RF antenna, etc.), and so forth.

Aspects of the present disclosure may be embodied as a system, method or computer program product. Furthermore, aspects of the present disclosure may take the form of a computer program product embodied in one or more computer readable medium(s) having computer readable program code embodied thereon.

In some desirable embodiments, a thermal contrast therapy system (which may be a subset of thermal therapeutic wraps) includes the following attributes: it provides rapid switching from heating to cooling; it has programmable temperature and time cycles, it provides cyclical compression without irritating noise, cyclical compression may be programmable, it is lightweight enough to be easily carried and may be carried inconspicuously, and it includes a built-in sterilizer mechanism to treat its fluid loop(s). In addition, a unit according to some modes of the present invention is capable of rapid transition between heating and cooling and provides compression without noisy compressors.

In the following sections, detailed descriptions of examples and methods of the disclosure will be given. The description of both preferred and alternative examples though thorough are exemplary only, and it is understood that to those skilled in the art that variations, modifications, and alterations may be apparent. It is therefore to be understood that the examples do not limit the broadness of the aspects of the underlying disclosure as defined by the claims.

FIG. 1 illustrates at a relatively high level of abstraction a system 100 to administer heating, cooling, and/or pressure therapy in accordance with some embodiment of the present disclosure. System 100 includes a thermal therapeutic wrap 101 coupled to a therapy control unit 103. Thermal therapeutic wrap 101 is illustrated affixed to a body part 105, such as an arm. However, thermal therapeutic wrap 101 may be fashioned or adaptable to fit or conform to be placed in proximity to a variety of body parts. For example, thermal therapeutic wrap 101 may be a wrap to surround a limb such as an arm (as illustrated in FIG. 1) or leg. Alternatively, thermal therapeutic wrap 101 may be a substantially flat thermal therapeutic wrap to be affixed to a shoulder blade or a back, or thermal therapeutic wrap 101 may be cap-shaped to fit on the head, and so forth. In some embodiments, thermal therapeutic wrap 101 may be flexible to accommodate being placed over a joint such as a knee or elbow and be able to flex as the joint is flexed.

According to the present invention, a thermal therapeutic wrap 101 may include multiple disparate parts that are assembled for the purpose of applying a therapy protocol including a change in a thermal dynamic and pressure dynamic to a specified area of a patient. In some embodiments, the multiple disparate components may include a boundary layer 101A, such as a sleeve, liner or other portion that provides an inner surface closest to a patient.

Thermal therapeutic wrap 101 may be coupled to a body part either securely or loosely. For example, a secure coupling may use straps to couple thermal therapeutic wrap 101 to a body part such as a lower back. A secure coupling may include snaps or a hook and loop fastener such as Velcro™ if thermal therapeutic wrap 101 is fashioned as a wrap around a limb. In contrast, thermal therapeutic wrap 101 may be loosely coupled if it merely rests upon a body part, such as a cap-shaped thermal therapeutic wrap 101 that may be placed on a head, or a thermal therapeutic wrap 101 that may be draped over a shoulder, and so forth. In other embodiments, thermal therapeutic wrap 101 may be adapted to be held in place by an external apparatus, e.g., if thermal therapeutic wrap 101 is placed inside a brace, or inside a compression sleeve, or the like.

Therapy control unit 103 may be used to interface with thermal therapeutic wrap 101. Therapy control unit 103 may include a physical control module 113 that provides physical stimulus to thermal therapeutic wrap 101 via line 121 and/or line 123. For example, therapy control unit 103 may include heaters and/or coolers to deliver a temperature-controlled fluid to thermal therapeutic wrap 101 (e.g., line 121) and receive fluid returned from thermal therapeutic wrap 101 (e.g., via line 123). Thermal therapeutic wrap 101 would include an internal fluidic coupling of line 121 to line 123, such that a closed loop may be formed with lines 121, 123 back to therapy control unit 103.

In some embodiments, additional types of physical stimulus may be provided, such as a pressure stimulus delivered to thermal therapeutic wrap 101 via lines 121 and 123, e.g., by use of a pump within physical control module 113 and a valve 124. The pump and valve may be used to create pressure within the fluid lines 121 123. The increased pressure may in turn cause increased compression force upon tissue around which the wrap is secured. The increased pressure may be accomplished via control unit 103 increasing pump performance. For example, a pump may be used to force increased fluid into line 121 and thereby increase pressure in the line.

In another aspect, a valve 124 may divert some fluid to return line 123 and/or the valve 124 may partially close a return line 123 to prevent fluid from returning and thereby increase pressure within the line. Either method alone or in cooperation may be used to increase an internal pressure of line 121, line 123, and within the internal fluidic coupling of thermal therapeutic wrap 101. If the internal fluidic coupling is constructed from an expandable material, the coupling would expand with pressure and the effect would be to deliver pressure to a wrapped body part, via a fluid hydraulic pressurized cuff.

Therapy control unit 103 further may include a sensor interface module 115, which may be used to monitor the application of stimulus to thermal therapeutic wrap 101. For example, if temperature-controlled stimulus is being provided to thermal therapeutic wrap 101, then sensor interface module 115 may measure one or both of: a temperature of thermal therapeutic wrap 101 and a temperature of a patient's body part 105. If pressure-controlled stimulus is being provided to thermal therapeutic wrap 101, then sensors 127 in communication with sensor interface module 115 may measure an internal pressure of thermal therapeutic wrap 101 and a feedback loop may provide for a correct level of pressure. In some embodiments, a pressure transducer 126 may determine an amount of pressure against a body part 105 and a fluidic pressure may be adjusted to bring the amount of pressure against the body part 105 in compliance with a prescribed protocol. A respective feedback loop for pressure against a body part and a temperature of a body part may be created to periodically or continually monitor conditions experienced by the body part and adjust that experience so that it will be in compliance with a prescribed protocol.

Temperature and pressure feedback sensors may be embedded within temperature thermal therapeutic wrap 101 in order to gather measurements used in the feedback loops. The sensors 127 also may enable logging and reporting of temperature and pressure changes during the treatment. For temperature thermal therapeutic wrap 101, the system can be used with a single fluid path thermal therapeutic wrap or a dual fluid path thermal therapeutic wrap, which provides separate loops for hot and cold. Furthermore, the dual fluid path thermal therapeutic wrap may be operated by flushing the "off" loop (i.e., either hot fluid loop or cold fluid loop depending upon the cycle) with compressed air, which serves the dual purpose of removing the "off" loop fluid and replacing it with compressed air for air compression. Air compression may thereby be used to apply a compression force to a treated body part.

Some embodiments include one or more sensors 127 to provide data descriptive of a condition related to thermal therapy, For example, a sensor may record skin temperature (e.g., an infrared thermocouple), a feedback sensor 127 to record pressure against skin (e.g., a pressure transducer), etc.

Embodiments may include a liner, such as a sleeve 130 (or other shape) with one or more sensors 127 positioned under a therapeutic wrap in order to take measurements closer to the skin. Sensors or their sleeves may be used with a thermal therapy device, and may be retrofitted to existing units. Sensors 127 may integrate a feedback loop to control a specific device, e.g., a temperature sensor may be used to control a heater. A liner may be agnostic to wrap type and be used with a variety of thermal therapy units and sleeves. Feedback provided by the liner and the sensors may be used to generate control signals.

Sensors 127 and/or their sleeves may be disposable, thus providing an additional income stream to a vendor. Disposability helps ensure that the sensors 127 and/or their sleeves are sterile or at least clean of biological traces of a previous usage. Sensors 127 and/or their sleeves may be designed to help guard the relatively more expensive wrap from direct human exposure or contact, thus facilitating usage of the wrap with another patient.

Sensors 127 and/or their sleeves may include a unique ID (e.g., a barcode, a hash code, an RFID code, etc.) associated with the patient and/or treatment. Sensors or their sleeves may include removable storage for the generated data, and may include a wireless communication interface (e.g., Bluetooth, Near Field Communications) to a user device for data transfer.

Therapy control unit 103 further may include a processor 111 to execute a control program stored within a memory (not illustrated) coupled to processor 111. For example, processor 111 may be programmed to provide a temperature-controlled therapy to thermal therapeutic wrap 101, according to a predetermined time versus temperature profile. The predetermined profile may be selected based upon an expected therapeutic benefit. In this example, processor 111 dynamically may control physical control module 113 to provide a fluid at a controlled temperature to thermal therapeutic wrap 101, and a measured feedback temperature may be received by sensor interface 115 via line 125. Processor 111 may then adjust its control of physical control module 113 in order to minimize a deviation of the measured feedback temperature from the predetermined time versus temperature profile.

A predetermined time versus a temperature profile may include control over one or more of: the number of cycles between hot and cold temperatures; the hot temperature; the cold temperature; the time spent at hot temperature; the time spent at cold temperature; a transition time and/or rate between hot and cold; a shape of cyclical transitions (e.g., like a sinusoid or like a square wave); relative ratios between hot and cold; flow rates (e.g., milliliters per second) of hot and cold; and so forth. In some embodiments, the predetermined time versus temperature profile may include may include only cycles of heating, or only cycles of cooling.

Lines 121, 123 and/or 125 may include electrical control lines to control elements within thermal therapeutic wrap 101, as discussed below in further detail in connection with FIG. 2. Although FIG. 1 illustrates lines 121, 123 and 125 functionally as separate lines, a physical implementation of lines 121, 123 and/or 125 may combine some or all of the functions of lines 121, 123 and/or 125 into a fewer number of physical lines.

Thermal therapeutic wrap 101 may be constructed from a flexible material that can conform at least partially to a body shape, e.g., by being wrapped around a limb or to fit snugly on a scalp. However, thermal therapeutic wrap 101 also may include a minimum level of stiffness in order to prevent pinching of internal fluidic channels. Thermal therapeutic wrap 101 may include a protective outer layer in order to protect internal fluidic channels from puncture damage or the like. Thermal therapeutic wrap 101 also may include an outer surface texture or material that is comfortable (or at least not uncomfortable) to human touch. The outer layer also should have high thermal transmissibility.

Figure 2:
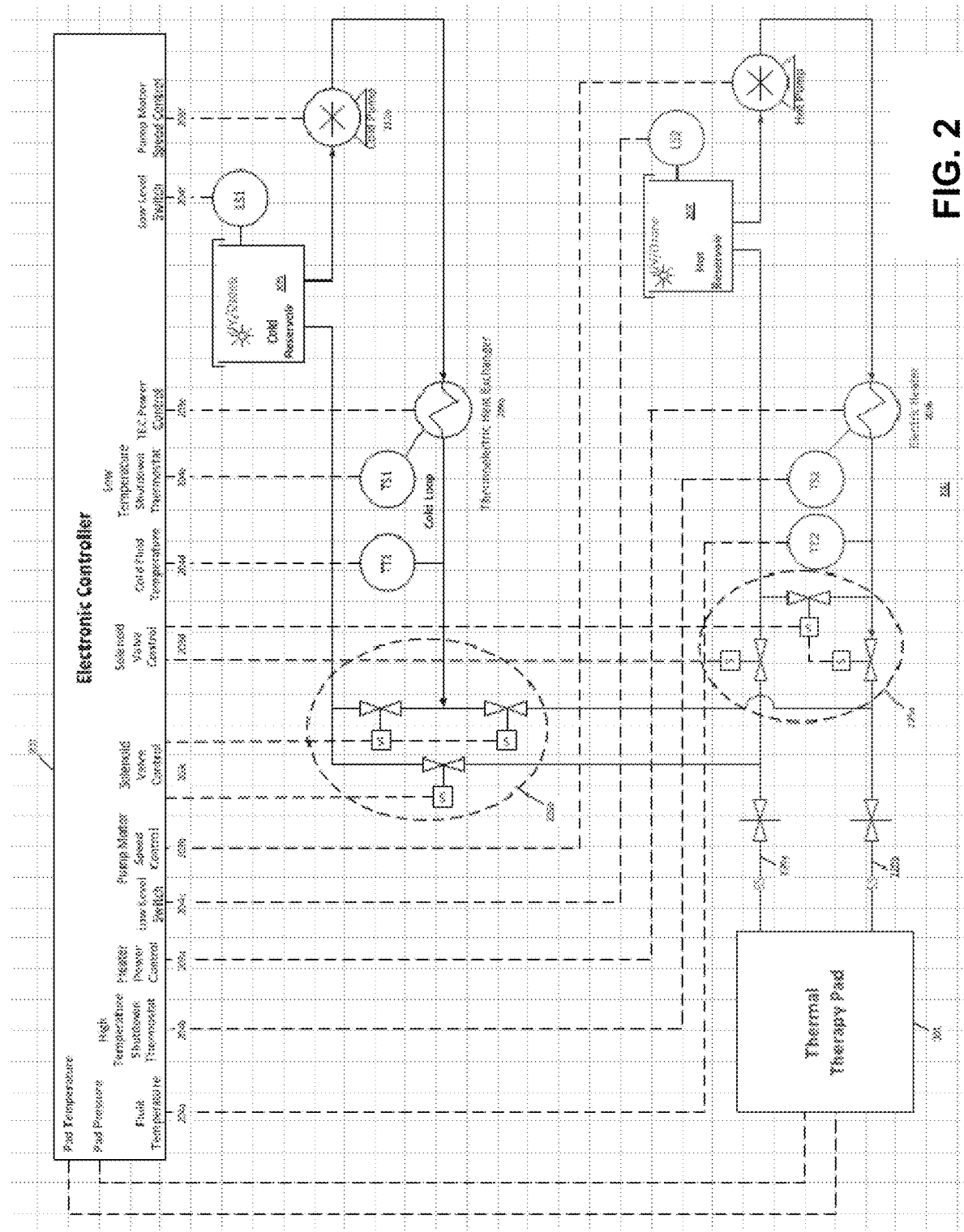
FIG. 2 illustrates a relatively lower level of abstraction a thermal contrast therapy system according to some exemplary embodiments of the present invention.

FIG. 2 illustrates at a relatively lower level of abstraction a system 200 to administer heating, cooling, and/or pressure therapy in accordance with some embodiment of the present disclosure. Components of system 200 are interconnected as shown in FIG. 2. System 200 includes electronic controller 202, which may correspond to therapy control unit 103 of FIG. 1. System 200 also may include thermal therapeutic wrap 201 (similar to thermal therapeutic wrap 101 of FIG. 1), a plurality of telemetric sensing or monitoring signals 204a . . . 204d (collectively, monitoring signals 204), and a plurality of control signals 203a . . . 203h (collectively, control signals 203). An individual but nonspecific monitoring signal or control signal may be referred to as a monitoring signal 204 or a control signal 203, respectively. FIG. 2 omits certain well-known features such as AC and/or DC power distribution.

A pair of fluidic lines 220a, 220b (collectively, fluidic lines 220) couple thermal therapeutic wrap 201 to other components of system 200. One of fluidic lines 220a, 220b may be an input line, and the other of fluidic lines 220a, 220b may be an output line. Fluidic lines 220a, 220b may be flexible and have a length of up to several feet, in order for thermal therapeutic wrap 201 to be located a short distance from the other components of system 200. For example, the other components of system 200 may be carried by a person (e.g., on a belt, in a backpack, in a "fanny pack", etc.), or be located a short distance away (e.g., on a table or equipment cart within about 5 feet of the person), while still allowing thermal therapeutic wrap 201 to be positioned substantially anywhere on the person.

In some embodiments, system 200 may be operable either from an AC line voltage or from battery power. A target minimum operating time on battery power is at least one hour.

System 200 further may include a hot fluidic line 221a, 221b (including its return, collectively hot fluidic lines 221) and a cold fluidic line 223a, 223b (including its return, collectively cold fluidic lines 223). A set of valves 225a may be used to control whether or not hot fluidic lines 221 are operationally coupled to fluidic lines 220. A similar set of valves 225b may control whether or not cold fluidic lines 223 are operationally coupled to fluidic lines 220. Hot fluidic lines 221 couple together hot fluid reservoir 207 and hot pump 211a. Cold fluidic lines 223 couple together cold fluid reservoir 205 and hot pump 211b.

System 200 further may include electronic controller 202. Electronic controller 202 may include several telemetric monitoring inputs 204a . . . 204f (collectively, monitoring signals 204). Examples of monitoring inputs 204 include temperature measurements of temperature sensitive or controlled elements such as fluidic lines 221, 223, thermoelectric ("TEC") heat exchangers 209a, 209b, and levels of reservoirs 205, 207.

Based upon a desired stimulus profile and measurements from monitoring inputs 204, electronic controller 202 may provide control signals 203a . . . 203f (collectively, control signals 203) to the remainder of system 200, in order to provide a desired stimulus to thermal therapeutic wrap 201. Examples of control signals 203 include valve controls 203c, 203d, TEC power control 203a, 203e, pump controls 203b, 203f, and so forth.

Some embodiments include an arrangement of valves and pumps as described in the drawings. In particular, a specific arrangement of valves and pumps to form a feedback loop maintaining temperature levels and facilitating accelerated transition of thermal fluid applied to treated area is novel over the known art.

According to the present invention fluid control devices, including, for example, an arrangement of pumps, fluid valves and fluid loops, may apply thermal fluid hydraulic pressure to cuff and/or wrap pressure without need for air pressure and associated pneumatic tubing. Furthermore, the hydraulic pressure when applied together with pneumatic pressure also is novel. Features and benefits include reduced size of the control unit, reduced noise level, cyclical compression without irritating noise, and simpler control units with no separate air channels.

In some embodiments, pressure from air or other gas within fluid channels that are not being used to provide fluid during a particular cycle. For example, air pressure may be provided in cold fluid channel 223b during circulation of heated fluid in a separate heated fluid channel 221b. The air is used to flush cold fluid out of the channel and may additionally provide compressive pressure of the wrap around a treated body part. Alternatively, air pressure may be used to flush hot fluid out of a channel. In this manner air may flush a first fluid prior to circulation of a second fluid.

Embodiments in accordance with the present disclosure may control system 100 and/or system 200 to provide a prescribed or desired therapy, including a controlled variation over time of the therapy. For example, prescribed variations of therapy may include at least one heated fluid loop (e.g., hot fluidic loop 221) and one chilled fluid loop (e.g., cold fluidic loop 223), which together may provide sequentially alternating hot and cold therapy to thermal therapeutic wrap 201 via alternating filling of hot fluidic loop 221 with heated fluid and filling chilled fluidic loop with chilled fluid. Some embodiments may provide additional temperature controlled loops and/or an unequal number of temperature controlled loops, such as two or more chilled fluid loops, two or more heated fluid loops, and so forth.

Usage of separate hot fluid reservoir 207 and cold fluid reservoir 205 is an improvement over the known art such as U.S. Pat. No. 9,345,614 ("the '614 patent"), which uses a single shared reservoir to supply fluid that in turn is either heated or cooled. The equilibrium temperature of the single shared reservoir in the '614 patent will be near the center of the temperature difference between hot fluid and cold fluid weighted by the ratio of hot versus cold fluid used. In contrast, usage of separate reservoirs in the present application allows for hot fluid reservoir 207 and cold fluid reservoir 205 to maintain respective separate equilibrium temperatures, each respective equilibrium temperature being closer to the respective temperature of the hot or cold fluid when applied as therapy in thermal therapeutic wrap 201. This means that less heating by TEC 209a or cooling by TEC 209b is required of the fluids drawn from hot fluid reservoir 207 or cold fluid reservoir 205, i.e., fewer joules of heat need to be added to hot fluid, or joules of heat removed from cold fluid. In turn, this means that TECs 209a, 209b may be one or more of smaller, less costly, draw less electrical power, and/or operate more quickly to bring fluid temperature to a required therapy temperature for thermal therapeutic wrap 201, compared to usage of a single shared fluid reservoir in the background art.

Another advantage of the present application compared to the background art is that switching of the set of hot valves 225a and the set of cold valves 225b may be sequenced and/or timed in such a way to minimize the flow and/or volume of fluid in a loop not being used during a specified period of time.

For example, when a heating, hot loop 221b is active and a flow of fluid in cold loop 223b is reduced. This provides several benefits compared to a single reservoir system of the background art. For example, unlike the background art, energy is not wasted by the thermal conditions in the respective loops not competing with each other. During a heat cycle valves may dictate that only heat is circulated through a thermal therapeutic wrap, and during a cooling cycle, only cool fluid is circulated through the thermal therapeutic wrap. In addition, in an ancillary aspect, repeatedly heating and cooling the valves themselves and the walls of dedicated loops 221b, 223b may be minimized via control of the valves. The temperature of fluid delivered to thermal therapeutic wrap 201 can be changed more quickly since there is less hot fluid needing to be cleared from the lines when cold therapy is now desired, and less cold fluid needing to be cleared from the lines when hot therapy is now desired. For example, the temperature of fluid delivered to temperature therapeutic wrap 201 may be changed, full range or near-full range, from a hot temperature to a cold temperature within 10-25 seconds.

Embodiments in accordance with the present disclosure may include a manifold controlled by solenoid valves, in order to connect one or more thermal therapeutic wraps 201 to fluid lines 221, 223. The solenoid valves may be operated to provide rapid switching between hot and cold fluids. In some embodiments, a valve timing sequence may be provided such that a return valve is closed later. The solenoids may be provided in different configurations, such as six one-way solenoids, or two three-way and two two-way solenoids, and so forth.

In some embodiments, separate pumps may be associated with each respective fluidic thermal lines 221, 223. Separate pumps may be useful to activate and to control more precisely the circulation of the temperature-controlled fluid (e.g., if placed before valves to control the combination of the fluid lines). Separate pumps and appropriate valve configuration also allow each of fluidic thermal lines 221, 223 to circulate independently of each other, without entering thermal therapeutic wrap 201, in order to better keep fluid in the respective reservoirs 205, 207 at the respective desired temperatures. In other embodiments, a single pump may be provided after the valves combining the hot and cold fluidic lines 221, 223. A single pump configuration may be smaller, lighter, and less costly, but may require more complicated valving in order to alternate maintenance of temperatures of reservoirs 205, 207.

Another advantage of the present application compared to the background art is that pumps 211a, 211b may be used to increase pressure in fluidic lines 221, 223 in order to deliver hydraulic pressure to thermal therapeutic wrap 201. The hydraulic pressure may then cause thermal therapeutic wrap 201 to expand and provide pressure against body part 105. In this situation, the elements providing pressure also are delivering thermal therapy, thus offering a possibility of more efficient transfer of heat or cold to body part 105 by the combination of pressure and direct contact by the fluid-bearing elements within thermal therapeutic wrap 201. In contrast, for the background art that uses air and an air compressor to inflate a cuff around a body part, such pneumatic methods do not necessarily provide an equivalent level of direct contact by the fluid-bearing elements within a thermal therapeutic wrap.

Another advantage of the present application compared to the background art is that usage of separate pumps 211a, 211b enables less complicated application of different pressure profiles of hot fluid and cold fluid, compared to a single pump configuration. For example, if it is desired that hot therapy should be delivered with 50% higher pressure than cold therapy, then hot pump 211a simply may be set to provide 50% more pressure than cold pump 211b, and no dynamic pressure control is required for pumps 211a, 211b. In contrast, for a single pump system, pressure provided by the single pump must be dynamically controlled in coordination with the desired temperature therapy profile.

Reservoirs 205, 207 are useful to provide rapid transfer between hot and cold fluid, by helping reduce a temperature differential that the heater and/or cooler need to provide. For example, if hot and cold fluid are alternately supplied to thermal therapeutic wrap 201, then as fluid of one temperature is supplied to thermal therapeutic wrap 201 (e.g., hot fluid), then the fluid of the other temperature (e.g., the cold fluid) may be recirculated to help maintain a desired temperature.

As illustrated in FIG. 2, each of fluidic lines 221, 223 may include a respective fluid reservoir 205, 207, with fluid level sensors, which feed one or more circulating pump(s). A temperature sensor may be used to measure the respective fluid temperature of each of fluidic lines 221, 223. Fluidic lines 221, 223 allow temperature-controlled fluid to recirculate through itself and/or flow through the thermal therapeutic wrap.

In some embodiments, hot fluidic line 221 may be in thermal communication with heaters (e.g., a thermoelectric (TEC) or resistive heater) to control its fluid temperature within a range, typically ranging from about 40 degrees C. to about 48 degrees C. Cold fluidic thermal line 223 may be in thermal communication with a cooler (e.g., a TEC cooler) to control its fluid temperature within a range, typically ranging from about 2 degrees C. to about 12 degrees C.

In some embodiments, fluidic lines 221 and 223 each may circulate within itself or through thermal therapeutic wrap 201 when coupled to a person. Electronic controller 202 may modulate power separately to the heaters and coolers in order to control a respective temperature of each loop. Temperature control may be based upon a proportional-integral-derivative ("PID") control algorithm and the measured temperature of the respective fluidic line.

In some embodiments, electronic controller 202 or a secondary controller (not illustrated in FIG. 2) may control solenoid valves that direct the hot and cold circulating fluids either to the therapeutic wrap or to recirculate within the loop.

In addition, cyclical compression as desired also may be provided. For example, the speed of each pump may be varied or modulated by use of the controller (i.e., either electronic controller 202 or the secondary controller if present) to provide cyclical compression. The user may specify a desired stimulus profile of hot fluidic loop 221 and cold fluidic loop 223. For example, electronic controller 202 may be programmed: to set respective desired temperatures of hot fluidic loop 221 and cold fluidic loop 223; to set respective time periods that hot fluidic loop 221 and cold fluidic loop 223 circulate through thermal therapeutic wrap 201, or recirculate without entering thermal therapeutic wrap 201, or no circulation at all; to set a number of hot/cold cycles each treatment performs; and to set a desired compression cycle at each temperature.

In some embodiments, an integrated sterilizer may sterilize fluid periodically or continuously in each reservoir in order to prevent bacteria growth. The sterilizer may use technology such as an ultraviolet ("UV") light source (including an UV light emitting diode ("LED")), or introduction of an ionized or reactive gas such as ozone, and so forth. The sterilizer may be located in reservoirs 206, 207, and/or along fluidic lines 221, 223. At least a portion of reservoirs 206, 207, and/or fluidic lines 221, 223 may be made from a UV-transmissive material in order to pass UV light for sterilization.

In some embodiments, a log or record of measured temperatures in system 200 and/or on the patient may be maintained for contemporaneous or post-treatment analysis. For example, patient temperatures may include a record temperature on skin during therapy, temperatures measured via infrared probe, bimetal sensor or other sensor.

In some embodiments, temperature measured from a patient (e.g., the patient's measured skin temperature) may be used as feedback to adjust operating parameters of system 200. For example, if skin probes indicate the patient's skin temperature is too high relative to a desired therapeutic profile, operation of system 200 may be adjusted to lower the temperature of hot fluidic line 221, or to reduce the amount of time that hot fluid is provided to thermal therapeutic wrap 201, or to increase the amount of time that cold fluid is provided to thermal therapeutic wrap 201, or to reduce the ratio of hot/cold operating time, and so forth, including a combination of methods.

In some embodiments, system 200 may be configured to provide an auditable record of control system operation, such as treatment time and date, patient data (e.g., measured skin temperature during treatment), therapy data (e.g., some or all of telemetric monitoring signals during treatment), compliance with a desired treatment profile, and so forth. In some embodiments, an interface to a remote web-based or cloud-based computing platform may be provided, at least to maintain the auditable record of control system operation.

In some embodiments, compression may be varied by varying speed of the pumped fluid. Pumped fluid speed may be varied by techniques such as: (a) controlling speed of the pump itself; (b) use of a pressure control orifice to set pressure levels; and/or (c) use of a pressure sensor to set pressure levels. At least some of these methods do not necessarily need to control speed of the pump itself. Sensors to measure speed and/or pressure of the pumped fluid speed may include a piezoelectric sensor in the thermal therapeutic wrap 201, and/or a fluid pressure sensor.

Figure 3:
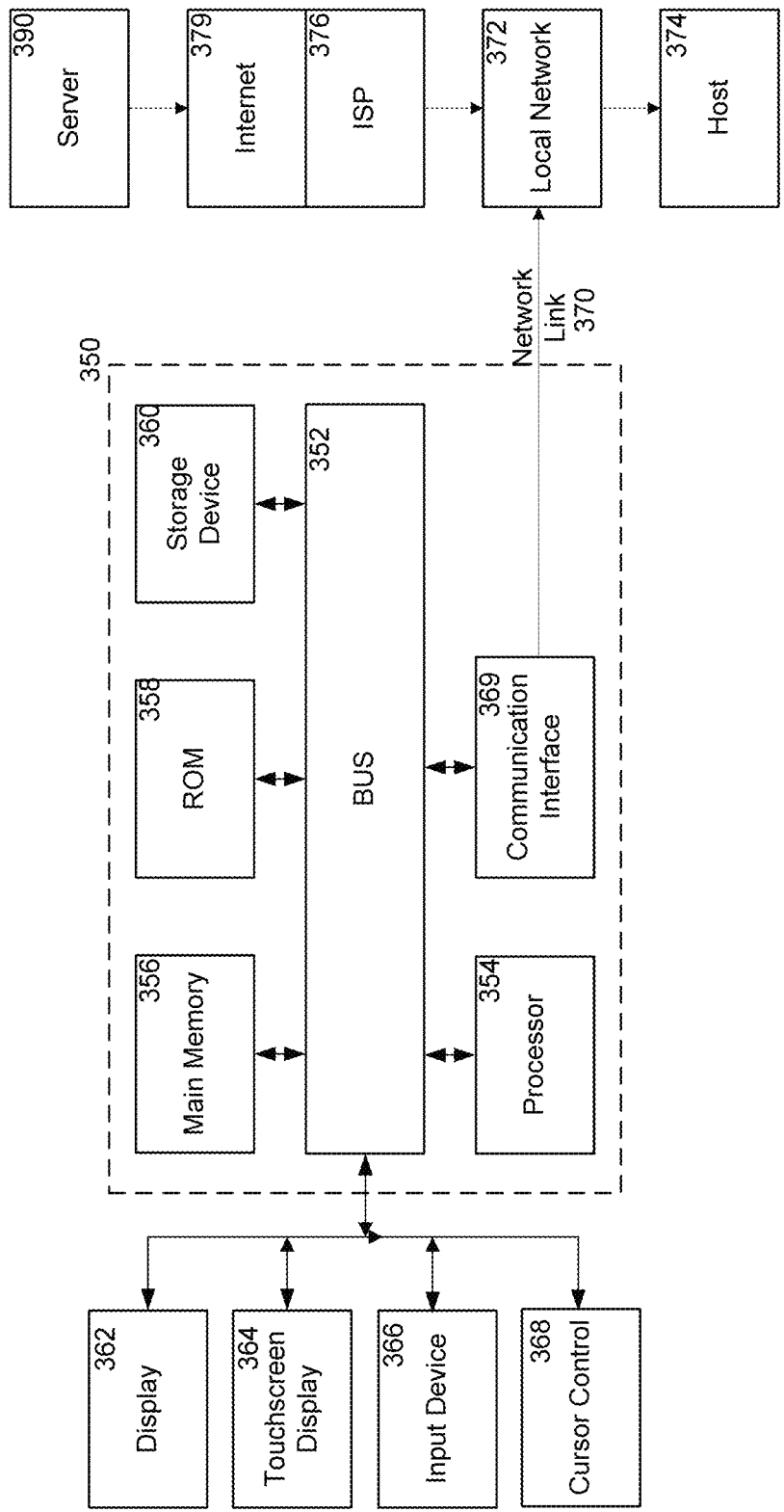
FIG. 3 illustrates a functional block diagram of a controller for a thermal contrast therapy system according to some exemplary embodiments of the present invention.

FIG. 3 illustrates a functional block diagram of a controller 350 in accordance with some embodiment of the present disclosure. Controller 350 may be useful to implement embodiments of the present invention, e.g., usable to function as at least part of electronic controller 202.

Controller 350 may include a bus 352 or other communication mechanism for communicating information, and a microcontroller 354 coupled with bus 352 for processing information. In some embodiments, bus 352 may represent more than one individual bus, e.g., a fast bus to access fast components such as main memory 356 and microcontroller 354, and a separate relatively slower bus to access slower components such as user interface devices (displays 362, 364, input device 366 and cursor control 368), storage device 360, and/or communication interface 369.

Controller 350 also includes a main memory 356, such as a random access memory (RAM) or other dynamic storage device, coupled to bus 352 for storing information and instructions to be executed by microcontroller 354. Main memory 356 may also be used for storing temporary variables or other intermediate information during execution of instructions to be executed by microcontroller 354. Controller 350 further includes a read only memory (ROM) 358 or other static storage device 360.

Controller 350 may be coupled via bus 352 to a display 362, such as a light emitting diode (LED) display, organic light-emitting diode (OLED), projector, or heads up display for displaying information to a computer user. An input device 366, including alphanumeric and other keys, may be coupled to bus 352 for communicating information and command selections to microcontroller 354. Another type of user input device is cursor control 368, such as a mouse, a trackball, a touchpad, or cursor direction keys for communicating direction information and command selections to microcontroller 354 and for controlling cursor movement on display 362. Another type of user input device is a touch-screen display 364 where a user may communicate information and command selections to microcontroller 354 by tactile interaction with the display thereby controlling cursor movement or alphanumeric and other keys. This input device typically has two degrees of freedom in two axes, a first axis (e.g., x) and a second axis (e.g., y), that allows the device to specify positions in a plane.

Embodiments of the invention are related to the use of controller 350 for setting operational parameters relating to operation of thermal therapeutic wrap 201. According to some embodiment of the invention, layering system parameters are defined and managed by controller 350 in response to microcontroller 354 executing one or more sequences of one or more instructions contained in main memory 356. Such instructions may be read into main memory 356 from another computer-readable medium, such as storage device 360. Execution of the sequences of instructions contained in main memory 356 causes microcontroller 354 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to microcontroller 354 for execution. Such a medium may take many forms, including but not limited to, non-volatile media, volatile media, and transmission media. Non-volatile media includes, for example, optical or magnetic disks, such as storage device 360 and 358. Volatile media includes dynamic memory, such as main memory 356. Transmission media includes coaxial cables, copper wire and fiber optics, including the wires that comprise bus 352. Transmission media may also take the form of acoustic or electromagnetic waves, such as those generated during radio wave and infrared data communications.

Common forms of computer-readable media include, for example, a SSD (solid state disk), a memory stick, hard disk or any other magnetic medium, a CD-ROM, any other optical medium, a RAM, a PROM, and EEPROM, any other memory chip or cartridge, or any other medium from which a computer may read.

Various forms of computer readable media may be involved in carrying one or more sequences of one or more instructions to microcontroller 354 for execution. For example, the instructions may initially be carried on a magnetic disk of a remote computer. The remote computer may load the instructions into its dynamic memory and send the instructions over a distributed network such as the Internet. A communication device may receive the data on the telephone line, cable line, or fiber-optic line and use an infrared transmitter to convert the data to an infrared signal. An infrared detector may receive the data carried in the infrared signal and appropriate circuitry may place the data on bus 352. Bus 352 carries the data to main memory 356, from which microcontroller 354 retrieves and executes the instructions. The instructions received by main memory 356 may optionally be stored on storage device 360 either before or after execution by microcontroller 354.

Controller 350 also includes a communication interface 369 coupled to bus 352. Communication interface 369 provides a two-way data communication coupling to a network link 370 that may be connected to a local network 372. For example, communication interface 369 may operate according to the internet protocol. As another example, communication interface 369 may be a local area network (LAN) card allowing a data communication connection to a compatible LAN. Wireless links may also be implemented. Network link 370 typically provides data communication through one or more networks to other data devices. For example, network link 370 provides a connection through local network 372 to a host computer 374 or to data equipment operated by an Internet Service Provider (ISP) 376. ISP 376 in turn provides data communication services through the worldwide packet data communication network now commonly referred to as the "Internet" 379. Local network 372 and Internet 379 both use electrical, electromagnetic or optical signals that carry digital data streams. The signals through the various networks and the signals on the network link 370 and through communication interface 369, which carry the digital data to and from controller 350 are exemplary forms of carrier waves transporting the information.

In some embodiments, Controller 350 may send messages and receive data, including program code, through the network(s), network link 370 and communication interface 369. In the Internet example, a server 390 might transmit a requested code for an application program through Internet 379, ISP 376, local network 372 and communication interface 369.

Processor 354 may execute the received code as it is received, and/or stored in storage device 360, or other non-volatile storage for later execution. In this manner, controller 350 may obtain application code in the form of a carrier wave.

Access devices may include any device capable of interacting with controller or other service provider. Some exemplary devices may include a mobile phone, a smart phone, a tablet, a netbook, a notebook computer, a laptop computer, a wearable computing or electronic device, a terminal, a kiosk or other type of automated apparatus. Additional exemplary devices may include any device with a microcontroller executing programmable commands to accomplish the steps described herein.

A controller may be a programmable board such as an Arduino™ or Raspberry Pi™ microprocessor board, and/or one or more of: personal computers, laptops, thermal therapeutic wrap devices, mobile phone devices and workstations located locally or at remote locations, but in communication with the system. System apparatus may include digital electronic circuitry included within computer hardware, firmware, software, or in combinations thereof. Additionally, aspects of the invention may be implemented manually.

Apparatus of the invention may be implemented in a computer program product tangibly embodied in a machine-readable storage device for execution by a programmable processor and method actions may be performed by a programmable processor executing a program of instructions to perform functions of the invention by operating on input data and generating output. The present invention may be implemented advantageously in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object oriented programming language, or in assembly or machine language if desired, and in any case, the language may be a compiled or interpreted language. Suitable microcontrollers include, by way of example, a processor and memory combination.

Generally, a processor will receive instructions and data from a read-only memory and/or a random access memory. Generally, a computer will include one or more mass storage devices for storing data files; such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EEPROM and flash memory devices; magnetic disks such as, internal hard disks and removable disks; and CD ROM disks. Any of the foregoing may be supplemented by, or incorporated in, ASICs (application-specific integrated circuits).

In some embodiments, implementation of the features of the present invention is accomplished via digital computer utilizing uniquely defined controlling logic, wherein the controller includes an integrated network between and among the various participants in Process Instruments.

The specific hardware configuration used is not particularly critical, as long as the processing power is adequate in terms of memory, information updating, order execution, redemption and issuance. Any number of commercially available database engines may allow for substantial account coverage and expansion. The controlling logic may use a language and compiler consistent with that on a CPU included in the medical device. These selections will be set according to per se well-known conventions in the software community.

Figure 4:
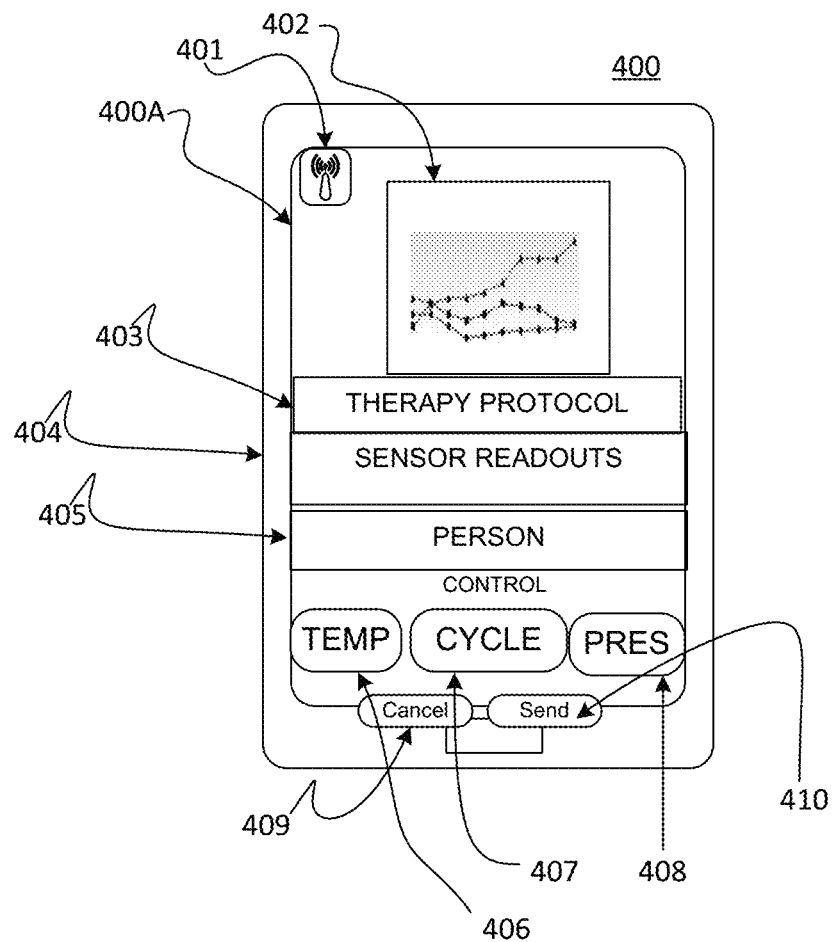
FIG. 4 illustrates a smart device and user interface according to some embodiments of the present invention.

Referring now to FIG. 4, a smart device 400 is illustrated with a human readable graphical user interface 400A. In some embodiments, a smart device 400 may be used to set parameters and protocols within a therapy control unit (not illustrated in FIG. 4). The smart device will typically communicate via an embedded wireless device 401 that may use a form of near field communication (such as IEEE 802.15.1 known as Bluetooth™, or IEEE 802.15.4 known as ZigBee™) to interact with the therapy control unit. Interactive user controls on the smart device may set therapy protocols 403, process sensor readings 404; identify a patient receiving therapy 405, or other functionality. In some embodiments, data 402 may be displayed for review by one or both of: a therapy provider and a patient. The data may include, for example, sensor readings at specified time intervals.

In another aspect, a smart device 400 may include control modules that allow for wireless control of one or more protocol parameters, such as: temperature settings 406; number of cycles and length of respective cycles 407; and an amount of pressure 408 to accompany the respective cycles. In addition, a cancel control 409 may reset the smart device app and a "send" control 410 may wirelessly send one or more of: sensor readings 404, protocol parameters, date and time, location (via, for example GPS), a user identifier (such as an alphanumeric universally unique identifier UUID). The send button may communicate via a Wi-Fi, cellular network or other wireless platform.

Figure 5:
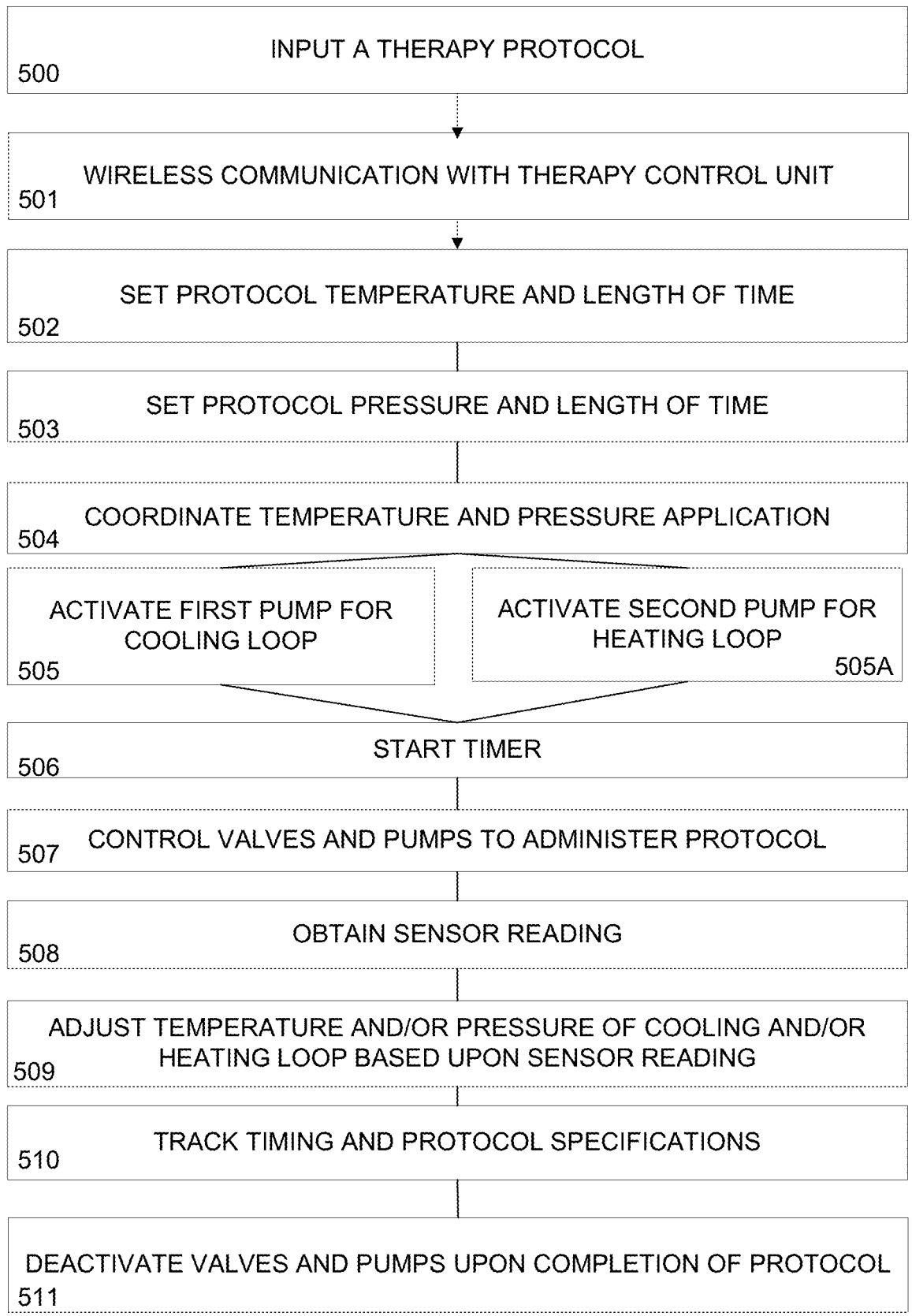
FIG. 5 illustrates method steps that may be implemented in some embodiments of the present invention.

Referring now to FIG. 5, method steps are presented that may be followed in whole or in part in various implementations of the present invention. At method step 500, a user or health care provider may input a therapy protocol. The therapy protocol may be entered into a therapy control unit, or via a smart device. At method step 501, in some embodiment's a therapy protocol may be entered remotely and transmitted to a therapy control unit via a network, such as one or more of: the Internet, via a cellular or wireless network and via near field communications.

At method step 502, a protocol temperature and length of time may be input. At method step 503, a protocol pressure and length of time may be set.

At method step 504, a temperature and pressure specified for a protocol may be coordinated. Coordination may include, for example, an amount of pressure that will be applied while an amount of heat or cooling therapy is simultaneously applied.

At method step 505, a first pump may be activated to control circulation of a cooling fluid. At method step 505A a second pump may be activated to control circulation of a heating fluid. One or both of method steps 505, 505A may be performed, either in sequence, or at least partially concurrently, or individually without the other of method steps 505, 505A. At method step 506 a timer may be started to associate a time that a protocol step or cycle is administered and at method step 507 one or more valves and pumps may be controlled to administer the therapy protocol input.

At method step 508, the therapy control unit may receive one or more sensor readings and at method step 509, the therapy control unit may adjust one or both of the cooling and heating loop based upon the sensor readings received.

At method step 510, timing of one or both of a heat cycle and a cooling cycle and an amount of pressure applied during the respective cycles may be tracked in accordance with the protocol specifications.

At method step 511, one or both of valves and pumps may be deactivated upon completion of the therapy protocol. Other method steps may be included and variations of those steps described above are all within the scope of the present invention.

Figure 6:
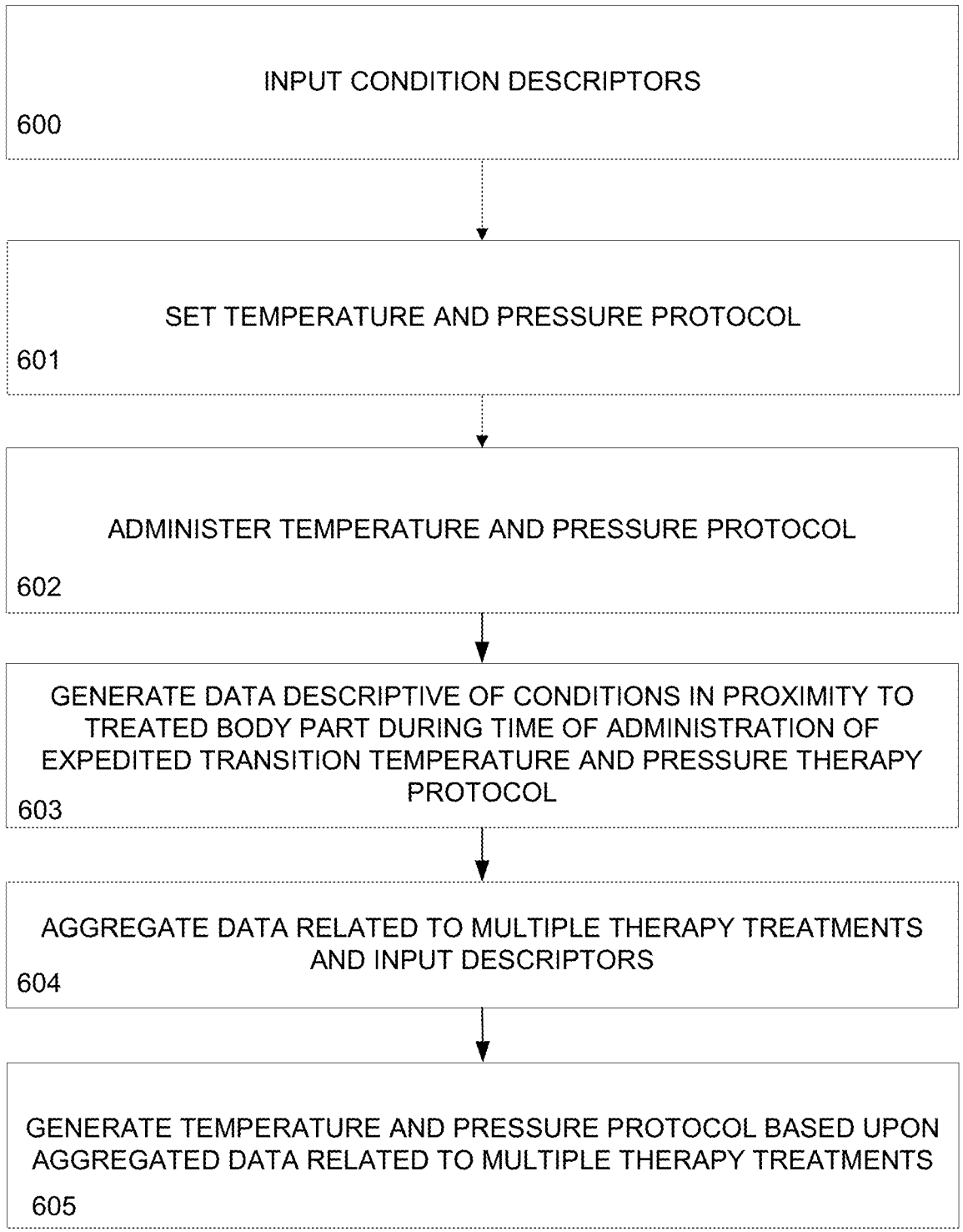
FIG. 6 illustrates additional method steps that may be implemented in some embodiments of the present invention.

Referring now to FIG. 6, additional method steps are listed that relate to aggregation of therapy treatment data and generation of therapy protocols based upon the aggregated data. At method step 600 a user or health care practitioner or therapy practitioner may input condition descriptors and at method step 601 set a temperature and a pressure protocol for a patient to receive. At method step 602, a patient may be administered a temperature and pressure protocol.

At method step 603, data that is descriptive of conditions in proximity to a treated body part during a time of administration of an expedited transition temperature and pressure therapy protocol.

At method step 604, data generated during the administration of the expedited transition temperature and pressure therapy is aggregated. In some preferred embodiments the data may be aggregated across multiple treatments including one or multiple patients.

At method step 605, a new, fast transition temperature and pressure protocol may be generated based upon the aggregated data and success patterns for treatments.

Figure 7:
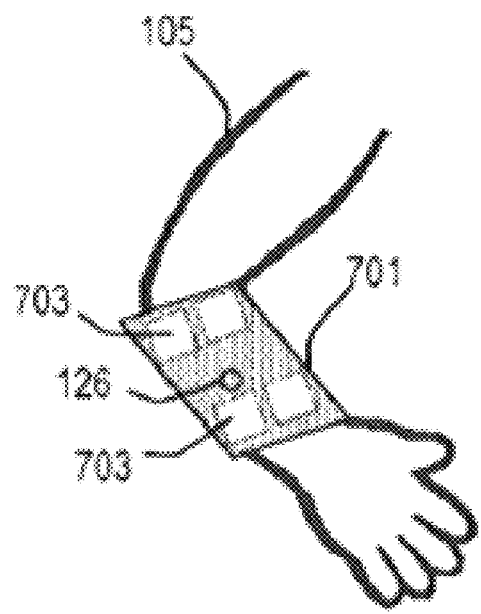
FIG. 7 illustrates a thermal therapeutic wrap according to an exemplary embodiment.

FIG. 7 illustrates an alternative embodiment 701 of a thermal therapeutic wrap. In particular, temperature therapeutic wrap 701 is similar to temperature thermal therapeutic wrap 101 and/or temperature therapeutic wrap 201, but further includes one or more integrated light therapy sources 703 (for sake of clarity, not all integrated light therapy sources are marked with a reference number in FIG. 7). Light therapy also may be known as phototherapy or heliotherapy, and may include exposure to specific wavelengths or ranges of wavelengths of light that are expected to provide a therapeutic benefit. The therapeutic benefit may include a proven clinical effect and/or a placebo benefit. The light may be administered for a prescribed amount of time and/or time of day (e.g., at night during sleep). Embodiments in accordance with the present disclosure combine light therapy with accelerated transition thermal contrast therapy in order to provide a more compact device 701 that is able to deliver both types of therapy to the same body part, and deliver the therapies simultaneously if desired.

Temperature therapeutic wrap 701 includes one or more integrated light therapy sources 703 that deliver the therapeutic light. Sources 703 are positioned in order to emit light toward a body part when temperature therapeutic wrap 701 is attached to the body part. Temperature therapeutic wrap 701 may differ from the depiction of FIG. 7, e.g., by usage of a different number of sources 703 or different placement of sources 703. In some embodiments, sources 703 may be dynamically controlled to provide light that varies over time in intensity, wavelength, or other characteristic. The light therapy may be combined with temperature and pressure therapy, either sequentially or at least partially at the same time.

In some embodiments, operation of the light therapy sources 703 may be coordinated with delivery of temperature and/or pressure therapy by temperature therapeutic wrap 701. As such, one or more light sources 703 may emit light either: a) independent of a temperature condition associate with the wrap; b) independent of a pressure condition associated with the wrap; c) in combination with a specific light therapy state; d) in combination with a specific pressure state and in combination with both temperature and pressure state caused b, or otherwise associated with the wrap.

Figure 8A:
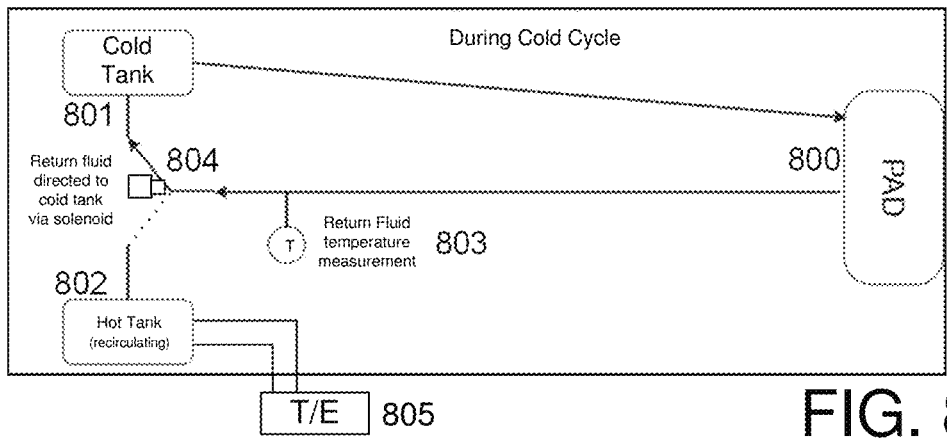
FIGS. 8A-8C illustrate exemplary states of fluid circulation through a thermal therapeutic wrap.
Figure 8B:
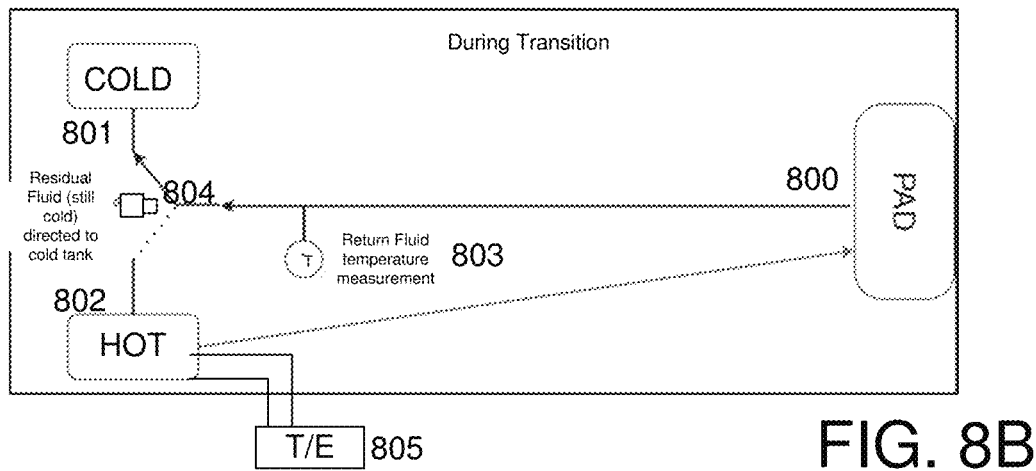
Figure 8C:
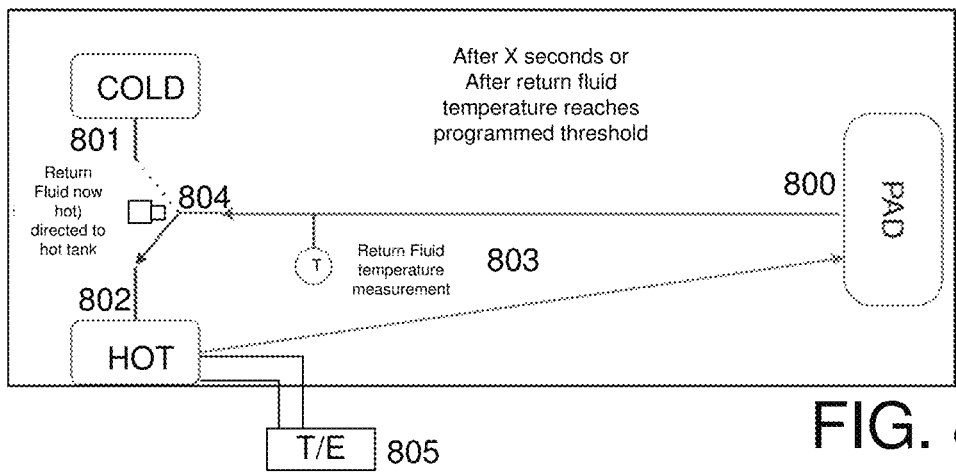
Figure 9A:
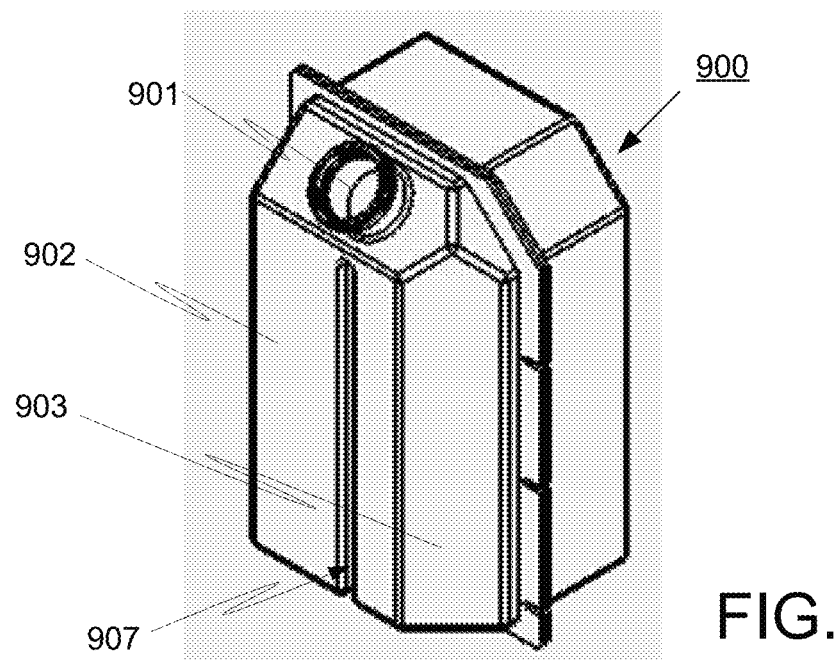
FIGS. 9A-9D illustrate various aspects of a fluid tank according to some embodiments of the present invention.
Figure 9B:
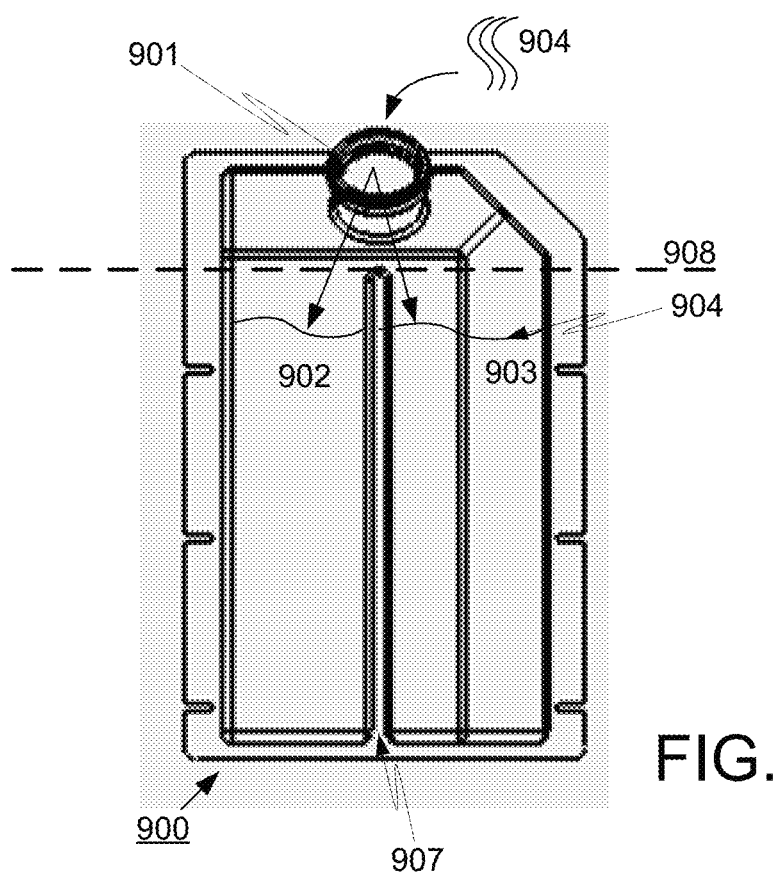
Figure 9C:
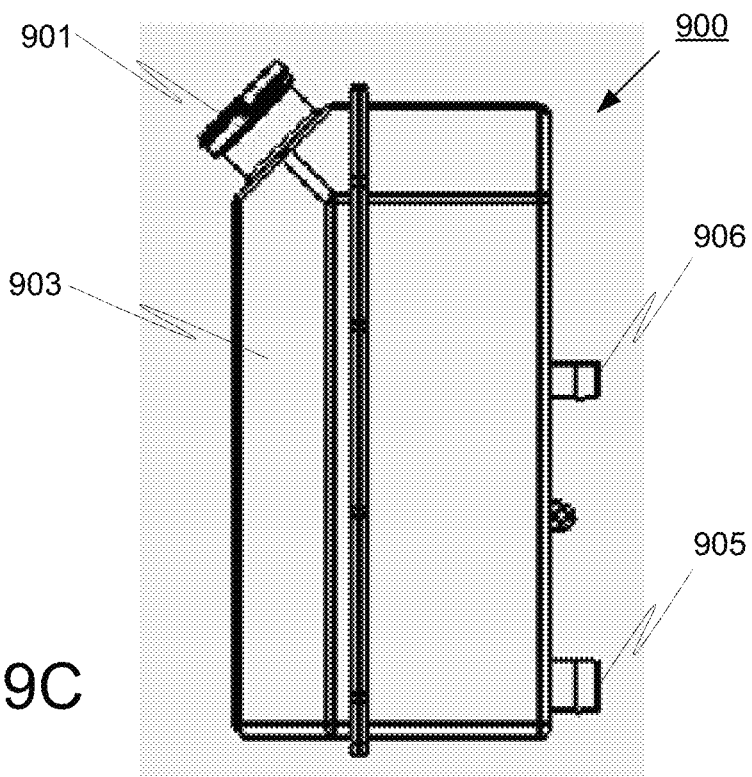
Figure 9D:
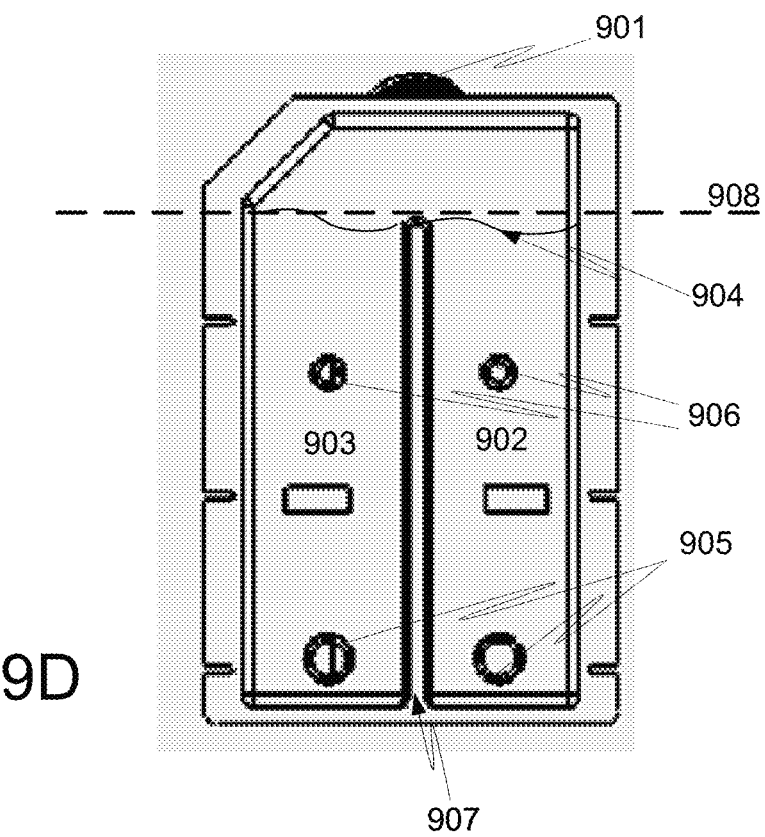

Referring now to FIGS. 8A-8C, block diagrams illustrate circulation of hot and cold fluid through a temperature therapeutic wrap 800. At 8A, during a temperature cycle circulating cold fluid through a temperature therapeutic wrap 800 (Cold Cycle). During a Cold Cycle, a solenoid 804 directs fluid returning from the temperature therapeutic wrap 800 (return fluid) to a cold fluid reservoir 801. A hot fluid reservoir 802 contains fluid that is kept at a raised temperature level (as compared to a temperature of the cold fluid). The temperature level of one or both of the hot fluid and cold fluid may be set and maintained via a thermoelectric temperature control unit 805. A temperature of one or more of the return fluid, fluid in the cold fluid reservoir 801 and fluid in the hot fluid reservoir 802 may be measured via a temperature sensor 803.

At FIG. 8B, during transition from a Cold Cycle to a period of time in which fluid that has been heated flows through the temperature therapeutic wrap 800 (Warm Cycle), a temperature of a residual fluid may be measured via the sensor 803. If the temperature measurement is below a threshold temperature specification, the residual fluid is directed via actuation of a solenoid 804 to the Cold fluid reservoir 801.

At FIG. 8C, upon reaching a threshold temperature measurement, the present invention provides that a return fluid may be directed to a hot fluid reservoir 802. The return fluid may be directed via actuation of the solenoid 804, a valve or other fluid direction control device. Fluid from the Heated Reservoir may be in thermal communication with a thermoelectric device 805 and brought to a controlled temperature via thermal communication with a Peltier device, a heater element or other heating mechanism. Direction of the return fluid to either of the Heated Fluid Reservoir and the Cold Fluid Reservoir may be accomplished after a timed delay (such as, for example, 10 or more seconds) or after the return fluid reaches a programmed or predetermined threshold temperature. Predetermination may be accomplished, for example via a mechanical thermostat actuated via a thermal spring.

Referring now to FIGS. 9A-9D, multiple various views of a thermal fluid reservoir unit 900 are illustrated. According to the present invention, a thermal fluid reservoir unit 900 may include both a Hot Fluid Reservoir 902 and a Cold Fluid Reservoir 903. The Hot Fluid Reservoir 902 and a Cold Fluid Reservoir 903 may both be filled via a single filling spout 901. Accordingly, thermal fluid 904 may be poured, or otherwise provided to, the single filling spout 901 and then diverted to one or both of the heated fluid reservoir 902 and the cold fluid reservoir. A tank dividing wall 907 may separate the Hot Fluid Reservoir 902 and a Cold Fluid Reservoir 903. The tank dividing wall 907 may comprise a thermal insulating material and or be shaped to provide an air gap between the Hot Fluid Reservoir 902 and a Cold Fluid Reservoir 903.

Thermal fluid 904 in the thermal fluid reservoir unit 900 may naturally flow from one of the Hot Fluid Reservoir 902 and a Cold Fluid Reservoir 903 to the other upon reaching a level 908 equal to a top of the tank dividing wall 907. Thermal fluid within the thermal fluid reservoir unit 900 will therefore self-equilibrate and prevent overflowing of one of the Hot Fluid Reservoir 902 and a Cold Fluid Reservoir 903 while the other reservoir is less than full of thermal fluid. One or more first fluid ports 905 may be functional as an egress for thermal fluid 904 and therefore be functional to transport fluid out of the thermal fluid reservoir unit 900. One or more second fluid ports 906 may be functional as an ingress for thermal fluid 904 and therefore be functional to transport fluid into the thermal fluid reservoir unit 900.

Embodiments as described herein provide at least the following improvements over the known art. Embodiments may include multiple wraps specific to fluid channel/pump configurations. For example, after a baseball game, a pitcher may have a first wrap on a pitching arm, and a second wrap on a leg.

Embodiments may include usage of wraps providing additional functionality that may be used with existing thermal therapy units, e.g., pumps and valves, sensors, sleeves etc.

Embodiments may include multiple fluid loops within a single wrap, each fluid loop may have separately controlled pressure and/or temperature. In particular, wrap may be designed with specific areas of high/low pressure and high/low heat/cold. Control of individual specified areas of wrap, designs may include areas of heat in one portion of wrap and cold in another portion; areas of pressure in one area and areas of relief in another. For example, a single wrap around the upper arm may include a first pressure loop to provide a first amount of pressure and temperature therapy the bicep muscles, and a second pressure loop to provide a second amount of pressure and temperature therapy to triceps muscles.

Embodiments may include lines from a TEC unit to the wrap that includes both fluid channels and data conduits.

Embodiments may include pre-programmed thermal and/or pressure cycles on a per patient basis with patient identification, e.g., a finger scan or other biometric identifier (ID). In particular, therapy cycles may be controlled with respect to temperature profiles, pressure profiles, feedback loop and adjustment of individual specific aspects (i.e. pumps, valves, TEC unit) during therapy cycles, and compliance record of actual therapy applied.

Embodiments may record location, time, date, and/or duration of therapy on a per patient basis with patient identification, e.g., a finger scan, biometric ID, unique identifier, etc. Specific embodiments may include control by use of a smart device (e.g., iPhone® or Android™ phone, tablet, etc.), and transmission to a data aggregator. In particular, embodiments may include aggregating data across multiple patients, location, age etc. Embodiments also may include remote control of therapy (e.g., therapy cycle profile being inputted by a practitioner from a remote site), and managing a universally unique identifier (UUID) of a therapeutic device.

Embodiments may include hot and/or cold temperature profiles according to a desired treatment plan on a per-patient basis with patient identification, e.g., finger scan, other biometric ID, unique identifier etc. In particular, profiles may include a therapy profile for injury, a profile to increase performance during sideline breaks of athletic performance, a profile to increase cognitive ability, and/or a profile to increase blood circulation during long sedentary periods, e.g., during airplane travel, sitting at a desk, laying in a hospital bed, etc.

Embodiments may include a built in sterilizer. Sterilization may be accomplished by use of ultraviolet light, chemical methods, ozone or other reactive gas, and/or a filter. Sterilization may be added to existing units by inserting a sterilizer in a fluid circulation loop, e.g., hot loop 221b and/or cold loop 223b.

Embodiments may combine temperature and/or pressure therapy with light therapy. In particular, light therapy may be applied in coordination with a thermal/pressure cycle, and/or to complement the objective of a thermal/pressure cycle. For example, a thermal/pressure cycle that heats and causes vasodilation may be complemented with light that also causes vasodilation, or the light may be removed during constriction thermal cycle, etc. Light therapy may increase adenosine triphosphate (ATP) production in synchrony with thermal cycle and/or pressure cycle. Light therapy may be applied at infrared, e.g., a wavelength of about 660-980 nanometers.

Embodiments may include magnetic application, and may be included in the thermal fluid being circulated. Light or magnetic therapy may be aligned with acupressure and/or acupuncture locations. The location of light or magnetic therapy may be detailed on a sleeve. The sleeve may be specific to a patient, so that a practitioner may mark a location of a therapeutic agent on a sleeve, and then therapy is applied according to the markings.

Embodiments may also include a therapeutic profile based upon biometric readings of a patient. This feature may be tied to activation of specific pumps, valves, etc. Parameters to monitor may include pulse rate, blood pressure, swelling, skin temperature, body temperature, temperature differential between skin and core body, and so forth.

Further, embodiments may include multiple wraps on a single patient may be administered at once with a single TEC machine. The hydraulic and physical interface may be configured in parallel with "Y" fittings to circulate, and/or a manifold with separate on/off valves. Embodiments may include automatic control of valves. Alternatively, the hydraulic and physical interface may be configured to be serial, using fittings to extend a flow, e.g., to an ankle, a lower leg, an upper leg, a torso, a shoulder an arm, etc. Alternatively, an attachment mechanism may couple one pump to the next. The hydraulic and physical interface may include fluid communication, and physical fasteners such as a hook and loop fastener (e.g., Velcro™), snaps, etc.

Embodiments may include multiple patients treated with a single large TEC machine, in order to provide efficiency of scale, wherein one patient may receive cooling therapy while another patient simultaneously may receive heating therapy. When it is time for the temperature cycle to reverse, a valve may switch to change fluid flow.

Multiple patients may be treated in parallel, such that a control unit turns flow on or off to an individual patient or individual treatment area (or limited/fully open) depending upon conditions measured at individual patient or treatment area.

Embodiments may combine thermal, pressure, and light with pharmaceutical treatment. Synergistic benefits may include treatment timing (e.g., synchronization), coordinated dosage and duration. Embodiments take advantage of capillary constriction and dilation based upon thermal treatment. Treatments may be by topical application (e.g., transdermal based upon treatment site), or injection at site of therapy. Embodiments include treatment protocols based upon drug response to thermal, pressure, and light conditions, for example, a heat or light activated drug.

Embodiments may include topical gel or cream, in conjunction with optimized thermal, magnetic, and/or light transfer therapy. Embodiments may include pain relief, e.g., anesthesia such as lidocaine to reduce localized pain. Embodiments may include a therapeutic agent. Embodiments may include cleaning and germ treatment to preserve sterile integrity of equipment.

Embodiments combine contrast therapy with movement (i.e., physical therapy (PT)), which may include treatment before and/or after PT. Embodiments include tracking movement (e.g., accelerometer or image tracking), and matching movement and thermal application. Embodiments may record movement, biometrics, thermal condition, pressure, and/or other treatments as well as time, place, and patient, etc.

Embodiments may also include therapeutic wrap with Thermal electric tiles on a thermal therapeutic wrap. For example, TEC tiles may be controlled individually or only in pre-defined areas. Fluid channels may be used to disperse excess heat or cold. In this case, fluid is needed only to mitigate thermal changes or differences, not to supply therapeutic temperature, and benefits may include less fluid required. Embodiments may be associated with reservoirs of heated fluid and/or cooled fluid. Embodiments may be more efficient and provide a faster temperature transition. A gel and/or liner material or gel pack may be used to disperse heat/cooling.

Embodiments may include a smart device controller for a TEC unit. Embodiments may display specific conditions pre-programmed in the TEC unit, and display conditions of treated area (e.g., pressure, temperature). Embodiments allow for remote monitoring of actual conditions. Embodiments are not limited to thermal therapeutic wraps, but instead may be applicable to other TEC devices. Embodiments may gather data in local data form, convert the data to Internet Protocol (IP) messages, transmit the IP messages to a remote monitoring station or server, and at the remote monitoring station or server convert the IP messages back to display format for displaying to a person, Embodiments may record time/place, may perform remote monitoring of status, and may monitor compliance with a treatment protocol.

Embodiments may provide big data aggregation across multiple treatments and profiles. Big data is known in the art as extremely large data sets that may be analyzed computationally to reveal patterns, trends, and associations, especially relating to human behavior and interactions. As applied to therapy, big data aggregation may help identify beneficial treatment regimes.

Embodiments may be combined with physical therapy motion monitoring, e.g., motion monitoring of a limb, while the patient is upright, reclined, or supine. Embodiments may monitor compliance with a therapy protocol, and may allow the compliance to be viewed remotely, e.g., by a health care provider or by the patient.

Figure 10A:
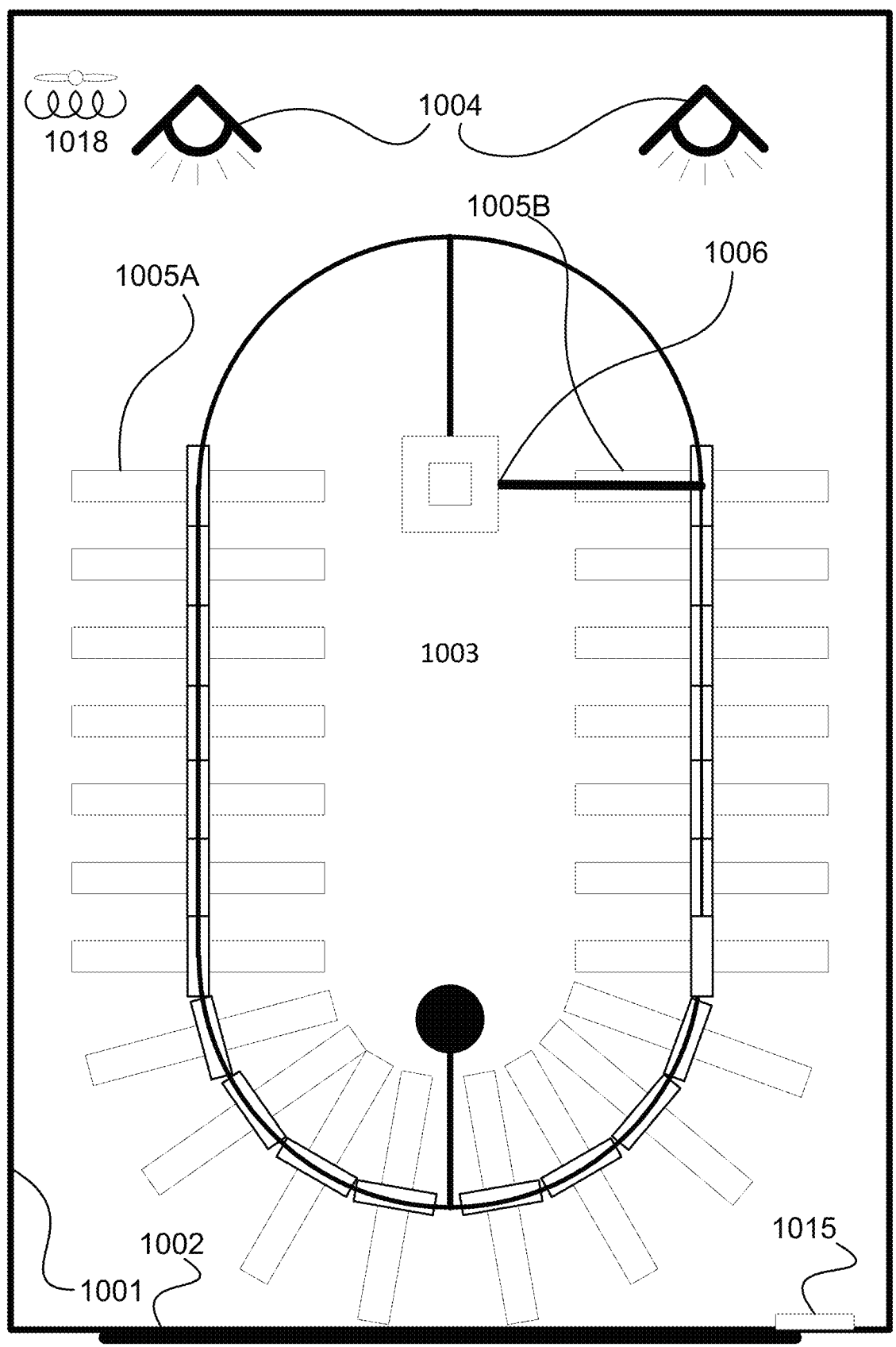
FIG. 10A illustrates a top-down plan view of the system for storing and sanitization thermal therapeutic wraps.

Referring now to FIG. 10A, a top-down view of the system for sanitarily storing thermal therapeutic treatment wraps is shown. For the sake of this discussion, a "wrap" or "treatment wrap" may include a boundary layer, such as those described above and including boundary layer 101A. An item processed according to the methods and apparatus described may include a thermal therapeutic wrap (including a thermal contrast wrap), a boundary layer, or both, but will be referred to generally as a wrap in this section. The system includes methods of use and apparatus including an enclosure 1001 with door 1002 for accessing an internal therapeutic wrap conveyor system 1003. In some embodiments, one or both of the enclosure 1001 and door 1002 may be opaque.

Thermal therapeutic treatment wrap 1005 may be attached to system 1003 by, among other things, a treatment hanger 1007. In some embodiments, system 1003 comprises a circular, polygonal, or other substantially closed shape allowing substantially cyclical motion with one or more wraps 1005 attached throughout. In exemplary embodiments, a series of wraps will be sanitized or otherwise have living biologics reduced.

Figure 10B:
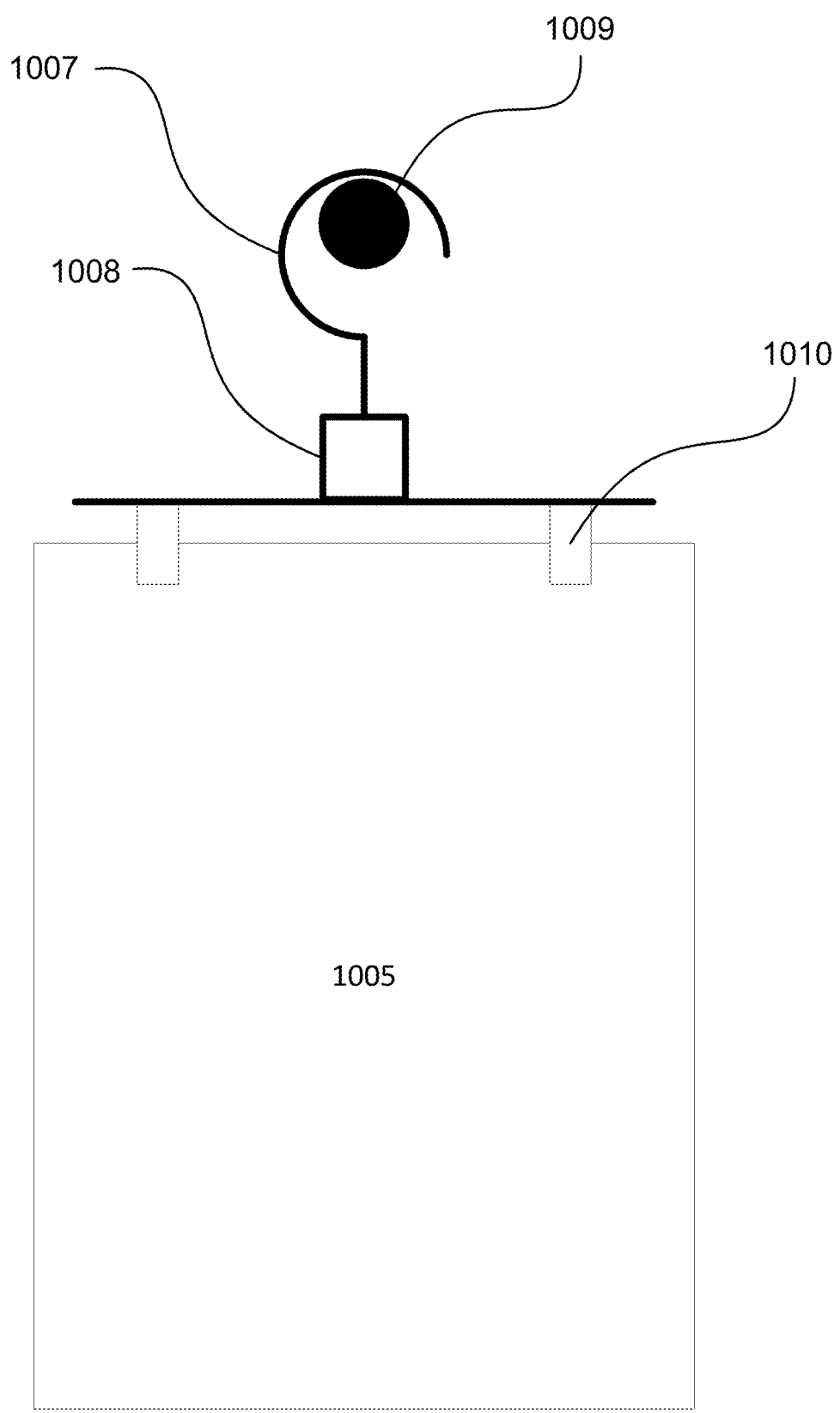
FIG. 10B illustrates an exemplary embodiment of a treatment wrap attached to the system by a hanger.

Referring now to FIG. 10B, an exemplary embodiment of a thermal therapeutic treatment wrap 1005 attached to system 1003 by a treatment hanger 1007 is shown. Treatment wrap hanger 1007 may be attached to system 1003 by treatment wrap hanger rod 1009, which may form an integral part of system 1003. In some embodiments, treatment wrap 1005 is attached to treatment wrap hanger 1007 by one or more hanger clips 1010. In some embodiments, treatment wrap spacer 1008 assists in ensuring an optimal placement of the treatment wrap 1005 relative to a biologic reduction apparatus. In some embodiments, a treatment wrap spacer 1008 associated with one wrap 1005 may push (or be pushed by) a treatment wrap spacer associated with a second wrap in the series forward or backward, thus facilitating movement of the two wraps.

Referring again to FIG. 10A, a sanitization source device 1004 (or other biologic reduction means) which may include, for example an environmental condition, such as a wavelength and intensity of light energy or other radiated energy, a chemical exposure, or a thermal condition, such as heat or cold capable of killing biologics, may be applied to the front side 1005A of wrap 1005. In exemplary embodiments, a biologic reduction means includes an sanitizing source device 1004. The sanitizing source device 1004 may emit other types of radiation, such as infrared or visible light, depending upon the application. Or the biologic reduction means may include a different stimulus capable of being applied to treatment wrap 1005 in a planar manner, such as a spray of a cleansing solvent. Once the front side 1005A of wrap 1005 has been exposed to the biologic reduction means for a period (which period may be a predetermined amount of time, a time based on environmental criteria, such as humidity, or a time based on sanitization or other biologic reduction indices associated with the treatment wrap 1005, such as a quantity of microbes per unit area), wrap indexing assembly 1006 may rotate treatment wrap 1005 about a central axis to expose rear side 1005B of treatment wrap 1005 to the sanitizing source device, such as an ultraviolet lamp. One or more air warmers 1018 may circulate warm air to keep wraps 1005 dry.

A user may access a wrap 1005 by opening door 1002. Opening door 1002 may, in some embodiments, trigger a proximity sensor 1015 or other mechanical means for recognizing that door 1002 is open. In exemplary embodiments, when proximity sensor 1015 is triggered, the sanitization or other biologic reduction means ceases application of the condition for reducing biologics. Thus, in the embodiment in which the sanitization or other biologic reduction means includes ultraviolet light, the ultraviolet light ceases, thus preventing any risk that the user is exposed to ultraviolet radiation.

Figure 10C:
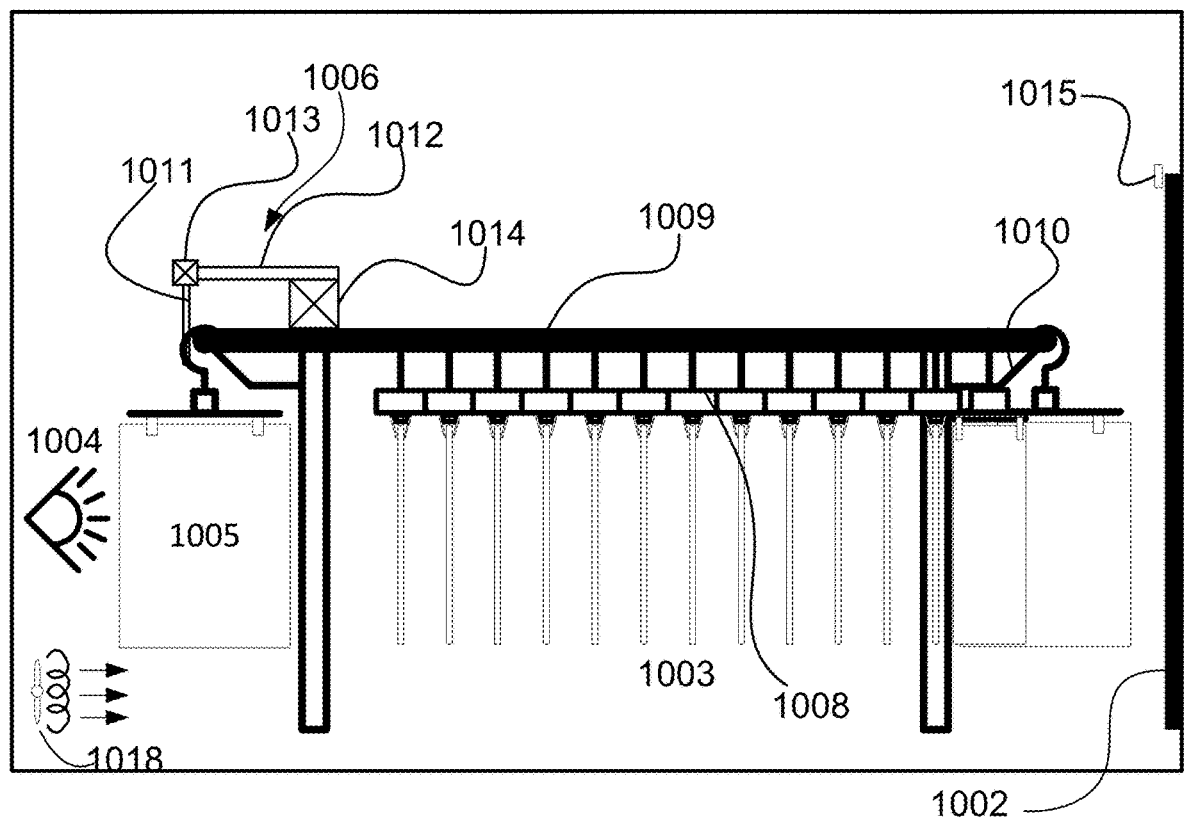
FIG. 10C illustrates a side view of the system.

Referring now to FIG. 10C, a side view of system 1003 is shown. This side view illustrates the wrap indexing assembly 1006. Wrap indexing assembly 1006 comprises an arm finger 1011, arm finger motor 1013, conveyor arm 1012, and conveyor arm motor 1014. After the sanitization or other biologic reduction period described above, wrap indexing assembly 1006 advances the series of wraps 1005. In some embodiments, this is achieved by one treatment wrap spacer 1008 pushing on the next treatment wrap spacer in the series of wraps. Once the move is complete, the finger lift motor 1013 may life arm finger 1011, and conveyor arm motor 1014 rotates conveyor arm 1012 to the next wrap facing the sanitization source device or other biologic reduction means. Finger lift motor 1013 may then lower arm finger 1011 to a point just behind the front-facing wrap's treatment wrap hanger 1007. The wrap indexing assembly 1006 may continue to index through wraps until the front and back of some or all wraps have been exposed to the sanitizing source device. In exemplary embodiments, this process may occur 1-6 times per day. However, it may be desirable to limit exposure time per wrap to provide sanitization or other biologic reduction without damaging the wrap material itself.

Figure 10D:
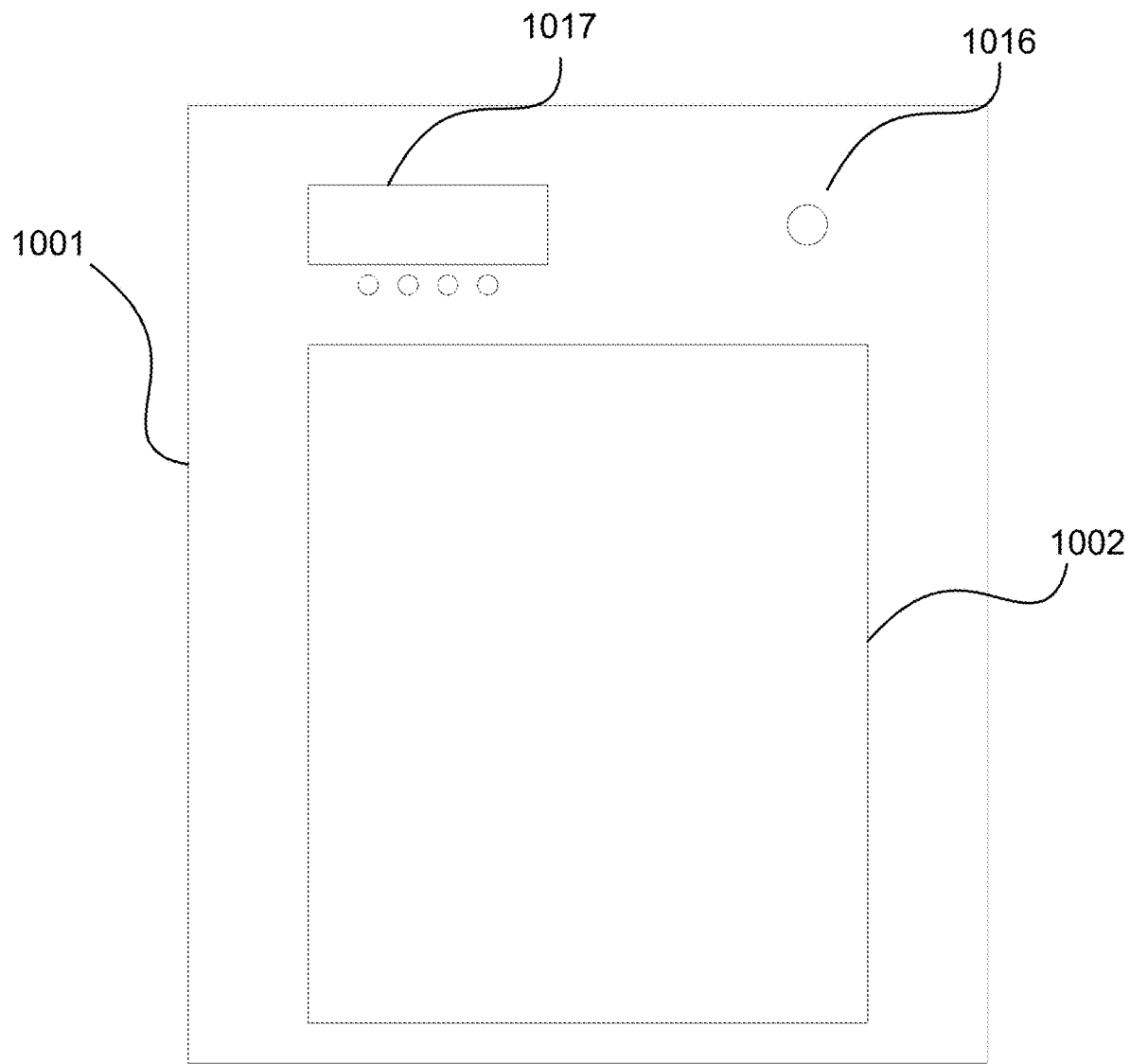
FIG. 10D illustrates the outside of the enclosure around the system.

Referring now to FIG. 10D, an exterior view of enclosure 1001, including door 1002, is shown. In some embodiments, a thermal therapeutic wrap advance button 1016 allows a user to manually advance the wrap indexing described above. Additionally, in some embodiments, a user interface 1017 may display useful information, such as number of wraps in enclosure 1001; sanitization or other metric for a presence of biologics, status of wraps in enclosure 1001; time of sanitization or other biologic reduction; time to completion of sanitization or other biologic reduction; and environmental conditions within enclosure 1001. User interface 1017 may also be used to configure aspects of the sanitization or other biologic reduction process, such as choosing a sanitization or other biologic reduction means where several are present; the temperature and duration of exposure to warm air from the air warmers; and the time of sanitization or other biologic reduction. User interface 1017 may include one or more user interface devices, such as buttons (as shown), a touch screen, or a separate application operable on a discrete device, such as a smart phone.

Figure 10E:
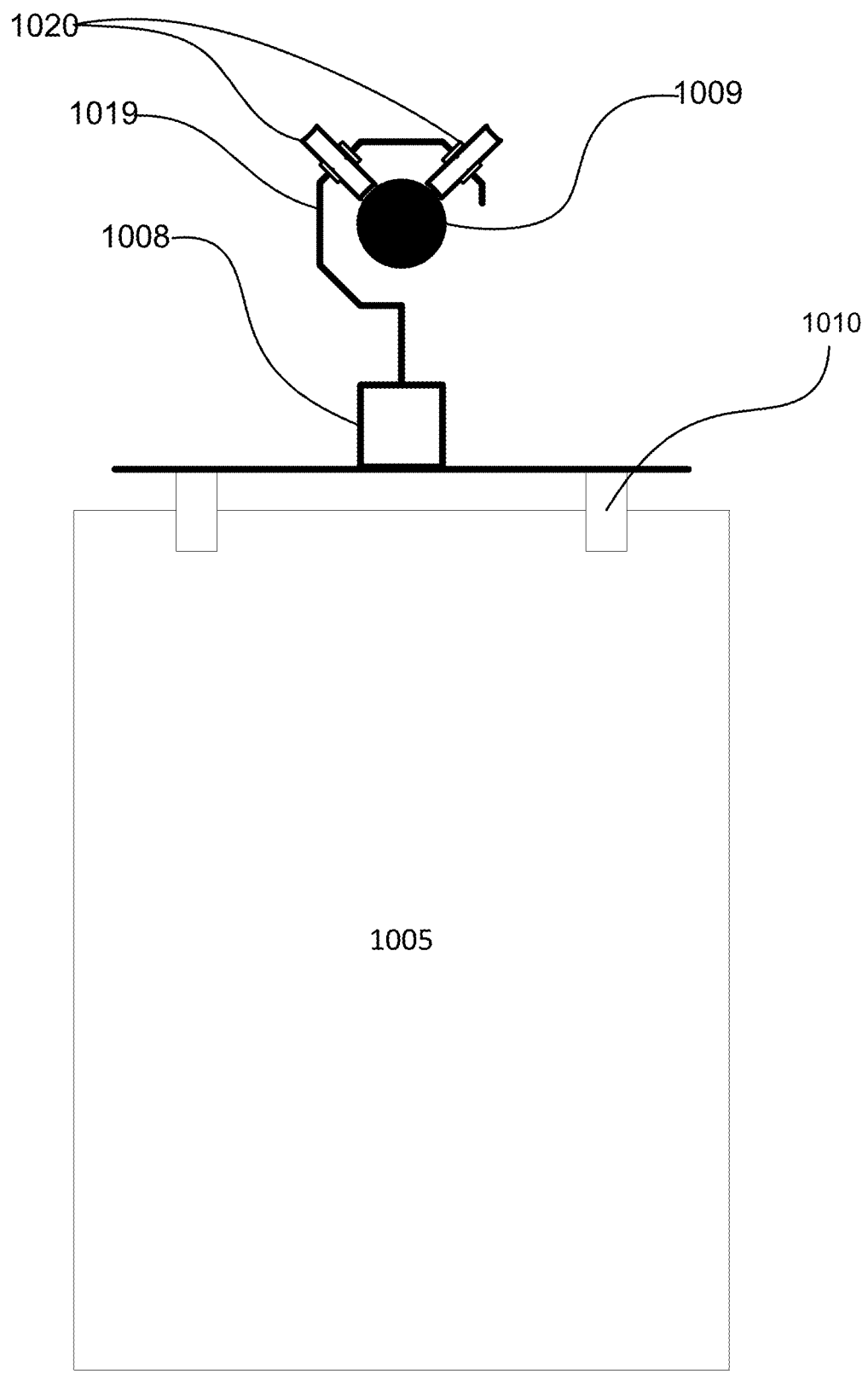
FIG. 10E illustrates an alternative embodiment of a thermal therapeutic wrap attached to the system by a hanger.

Referring now to FIG. 10E, an alternate method of attaching the treatment wrap to system 1003 is shown. In this embodiment, thermal therapeutic wrap hanger 1019 may be coupled to one or more pulley wheels for enhanced movement throughout the track within enclosure 1001.

Figure 11:
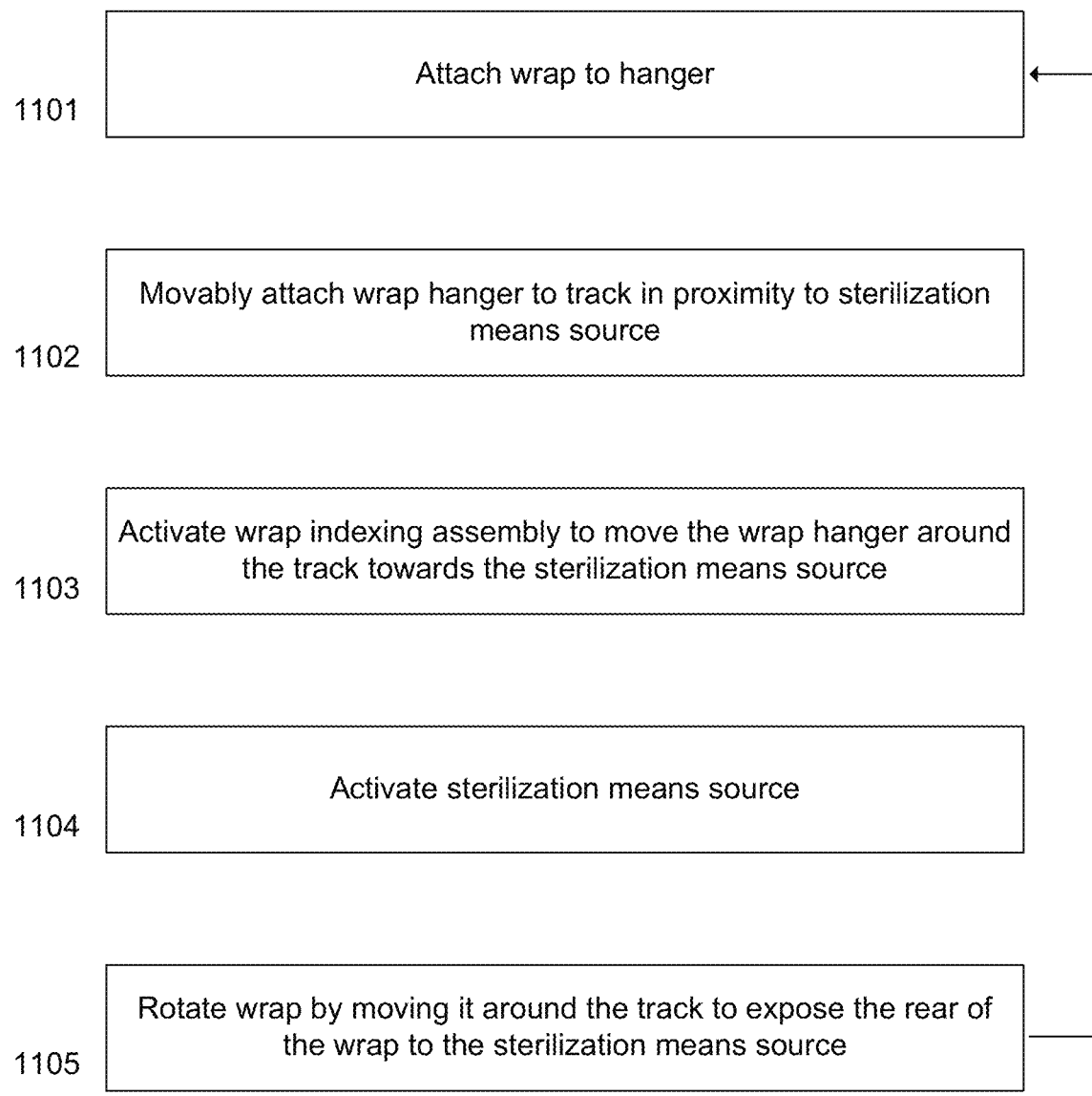
FIG. 11 illustrates an exemplary method for using the present system.

Referring now to FIG. 11, an exemplary method of using the present system is shown. At 1101, a wrap is attached to a wrap hanger. In some embodiments, this attachment is achieved by use of one or more hanger clips. At 1102, this wrap hanger is then movably attached to a track. The track may be in an enclosure and may be proximate to a sanitizing source device or other biologic reduction means source. In some embodiments, the sanitization or other biologic reduction means comprises ultraviolet light, and the sanitization or other biologic reduction means source comprises a device capable of emitting ultraviolet light, such as mercury vapor lamps or light-emitting diodes. In exemplary embodiments, this ultraviolet light may have a frequency between 255 nanometers and 280 nanometers.

At 1103, the wrap indexing assembly is operative to move the wrap toward the sanitization source device or other biologic reduction means source. At 1104, the sanitization source device or other biologic reduction means source is activated. For example, in the embodiment in which the sanitization or other biologic reduction means is ultraviolet light, light-emitting diodes may be activated. The wrap should be placed such that the ultraviolet light is not refracted or meaningfully split before reaching the wrap. At 1105, the wrap is moved around the track by the wrap indexing assembly to expose the rear of the wrap to the sanitization source device or other biologic reduction means source. (In exemplary embodiments, there are at least two sanitization source devices or other biologic reduction means sources within the enclosure.) In each case, each side of the wrap is exposed to the sanitization source device or other biologic reduction means for a certain amount of time, which may be predetermined or calculated based upon environmental factors or quality control factors. In exemplary embodiments, each side is exposed to the sanitization source device or other biologic reduction means for a period between ten seconds and five minutes.

Optionally, this method may be repeated. In exemplary embodiments, the method should be repeated between one and six times per day.

A number of embodiments of the present invention have been described. Nevertheless, it will be understood that various modifications may be made without departing from the spirit and scope of the invention. For example, various methods or equipment may be used to implement the process steps described herein or to create a device according to the inventive concepts provided above and further described in the claims. In addition, various integration of components, as well as software and firmware may be implemented. Accordingly, other embodiments are within the scope of the following claims.

While the foregoing is directed to embodiments of the present disclosure, other and further embodiments of the present disclosure may be devised without departing from the basic scope thereof. It is understood that various embodiments described herein may be utilized in combination with any other embodiment described, without departing from the scope contained herein. Further, the foregoing description is not intended to be exhaustive or to limit the disclosure to the precise form disclosed. Modifications and variations are possible in light of the above teachings or may be acquired from practice of the disclosure. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the disclosure unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A method for storing and reducing biologics on one or more thermal therapeutic wraps, the method comprising the steps of:
    attaching a thermal therapeutic wrap to a wrap hanger;
    movably attaching the wrap hanger to a track, wherein the track is in proximity to a sanitization source device and is within an enclosure comprising an exterior wall and a door;
    activating a wrap indexing assembly, which comprises a conveyor arm and a conveyor arm motor, wherein the conveyor arm motor is configured to rotate the conveyor arm, and the conveyor arm pushes the wrap hanger cyclically along the track;
    activating the sanitization source device to cause it to output a sanitation source; and
    exposing a first side of the wrap to the sanitization source device.

2. The method of claim 1, further comprising step of moving, using the wrap indexing assembly, the wrap to expose a second side of the wrap to the sanitization source device.

3. The method of claim 2, wherein the sanitization source device comprises a lamp operable to emit ultraviolet light.

4. The method of claim 3, wherein the first and second sides of the wrap are exposed to the lamp for a predetermined amount of time.

5. The method of claim 4, wherein the predetermined amount of time is between ten seconds and five minutes.

6. The method of claim 3, wherein the sanitization source device comprises mercury vapor lamps.

7. The method of claim 3, wherein the sanitization source device comprises light-emitting diodes.

8. The method of claim 3, wherein the ultraviolet light has a frequency between 255 nanometers and 280 nanometers.

9. The method of claim 3, wherein the method is repeated between one and six times per day.

10. The method of claim 3, wherein the wrap hanger further comprises a thermal therapeutic wrap spacer.

* * * * *